US008348844B2

(12) United States Patent
Kunjan et al.

(10) Patent No.: US 8,348,844 B2
(45) Date of Patent: Jan. 8, 2013

(54) AUTOMATED BLOOD SAMPLER AND ANALYZER

(76) Inventors: Kislaya Kunjan, Indianapolis, IN (US); Frank Perry Lloyd, Jr., Indianapolis, IN (US)

( * ) Notice: Subject to any disclaimer, the term of this patent is extended or adjusted under 35 U.S.C. 154(b) by 928 days.

(21) Appl. No.: 12/326,857

(22) Filed: Dec. 2, 2008

(65) Prior Publication Data

US 2010/0137778 A1 Jun. 3, 2010

(51) Int. Cl.
*A61B 5/00* (2006.01)

(52) U.S. Cl. ........................................................ 600/366

(58) Field of Classification Search ........................ None
See application file for complete search history.

(56) References Cited

U.S. PATENT DOCUMENTS

| | | | | |
|---|---|---|---|---|
| 2,797,149 | A | 6/1957 | Skeggs | |
| 4,077,395 | A | 3/1978 | Woolner | |
| 4,573,968 | A | 3/1986 | Parker | |
| 4,784,157 | A | 11/1988 | Halls et al. | |
| 4,796,644 | A | 1/1989 | Polaschegg | |
| 5,048,537 | A | 9/1991 | Messinger | |
| 5,148,811 | A | 9/1992 | Messinger | |
| 5,641,405 | A | 6/1997 | Keshaviah et al. | |
| 5,685,835 | A | 11/1997 | Brugger | |
| 5,687,718 | A | 11/1997 | Fischer et al. | |
| 5,697,899 | A | 12/1997 | Hillman et al. | |
| 5,758,643 | A | 6/1998 | Wong et al. | |
| 5,772,608 | A | 6/1998 | Dhas | |
| 5,902,253 | A | 5/1999 | Pfeiffer et al. | |
| 5,948,251 | A | 9/1999 | Brugger | |
| 6,017,318 | A | 1/2000 | Gauthier et al. | |
| 6,685,664 | B2 | 2/2004 | Levin et al. | |
| 6,736,783 | B2 | 5/2004 | Blake et al. | |
| 6,871,660 | B2 * | 3/2005 | Hampsch | 137/1 |
| 7,162,290 | B1 | 1/2007 | Levin | |
| 7,311,689 | B2 | 12/2007 | Levin et al. | |
| 7,314,452 | B2 | 1/2008 | Madonia | |
| 7,367,942 | B2 | 5/2008 | Grage et al. | |
| 7,445,604 | B2 | 11/2008 | Cash | |
| 7,608,042 | B2 | 10/2009 | Goldberger et al. | |
| 7,713,226 | B2 | 5/2010 | Ash et al. | |
| 7,860,543 | B2 | 12/2010 | Sterling et al. | |
| 2001/0049486 | A1 | 12/2001 | Evans et al. | |
| 2006/0009727 | A1 | 1/2006 | O'Mahony et al. | |
| 2006/0122536 | A1 | 6/2006 | Haar et al. | |
| 2006/0229531 | A1 | 10/2006 | Goldberger et al. | |
| 2007/0129618 | A1 | 6/2007 | Goldberger et al. | |
| 2007/0179435 | A1 | 8/2007 | Braig et al. | |
| 2007/0191716 | A1 | 8/2007 | Goldberger et al. | |
| 2007/0225675 | A1 | 9/2007 | Robinson et al. | |
| 2007/0240497 | A1 | 10/2007 | Robinson et al. | |
| 2007/0244381 | A1 | 10/2007 | Robinson et al. | |
| 2007/0244382 | A1 | 10/2007 | Robinson et al. | |
| 2008/0014601 | A1 | 1/2008 | Goldberger et al. | |
| 2008/0097288 | A1 | 4/2008 | Levin et al. | |
| 2008/0108942 | A1 * | 5/2008 | Brister et al. | 604/118 |
| 2009/0156922 | A1 | 6/2009 | Goldberger et al. | |
| 2009/0156975 | A1 | 6/2009 | Robinson et al. | |
| 2010/0020309 | A1 | 1/2010 | Goldberger et al. | |
| 2010/0114002 | A1 | 5/2010 | O'Mahony et al. | |

OTHER PUBLICATIONS

Kislaya Kunjan, M.S., M.B.A., and Frank P. Lloyd, Jr., M.D., Automated Blood Sampling and Glucose Sensing in Critical Care Settings, Journal of Diabetes Science and Technology, Mar. 2008, 194-200, vol. 2, Issue 2, Diabetes Technology Society, United States.

* cited by examiner

*Primary Examiner* — Kenneth R. Horlick
*Assistant Examiner* — David Thomas
(74) *Attorney, Agent, or Firm* — James Minerve

(57) ABSTRACT

An automated blood sampler integratable with a glucose monitor comprises a catheter connected to a tube-set forming a single blood passageway; a clamp-on air-bubble sensor and a occlusion sensor externally attached to the tube set; a single peristaltic pump and two 3-way pinch valves attached to the tube set and control fluid flow. The sampler draws blood from a stationary patient, samples the blood for analytical measurement of blood parameters; after which the passageway is rinsed, the blood re-infused, and slow saline infusion prevents vein collapse. The cycle repeats at user or predefined intervals. In another preferred embodiment, blood is not re-infused, and only one 3-way pinch valve is used.

25 Claims, 19 Drawing Sheets

Title: AUTOMATED BLOOD SAMPLER AND ANALYZER
Name of Applicants: Kislaya Kunjan and Frank P Lloyd Jr.

BD Insyte Autoguard Shielded IV Catheter

BD Saf-T-Intima Closed IV Catheter with Y-adapter

Piezo-Motor Based Pinch Valve

Title: AUTOMATED BLOOD SAMPLER AND ANALYZER
Name of Applicants: Kislaya Kunjan and Frank P Lloyd Jr.

Rear view of the Automated Strip feeder

Touch Screen Based Control System

Automated Blood Sampling Module
[Peristaltic Pump and Pinch Valves]

Automated Strip
Feeding Module

AUTOMATED BLOOD SAMPLER AND ANALYZER

CROSS REFERENCE TO RELATED APPLICATIONS

This application makes reference to Provisional Application 60/856,456 and Non provisional application Ser. No. 11/982,565.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

REFERENCE TO A SEQUENCE LISTING

Not Applicable

BACKGROUND OF THE INVENTION

1. Field of the Invention

This invention relates generally to systems and methods for monitoring blood constituents, and in particular, to improved methods and systems for integrating a blood monitoring system with a vascular sampling system for periodically measuring blood analytes and parameters using electrochemical, photochemical, optical techniques or a combination of the above techniques.

2. Description of Related Art

Tight glycemic control has been associated with better clinical outcomes in critical care settings. There are a number of inventions devoted to sampling, measuring, and/or regulating blood glucose levels of patients in ICU and undergoing surgery. The inventions comprising this field generally perform one or more of these functions independently or in a few cases integrate with other devices to provide a closed loop composite system that regulates blood glucose. This field is teeming with improvements by the inventors who are generally groups of professional engineers and physicians, constantly attempting to design improvements to the prior art in order to innovate a system that hospitals and physicians will embrace widely. Heretofore, none of the so called “closed loop” systems, which sample, measure, and administer medicine to adjust blood glucose levels, enjoy popular use. As will be pointed out below, many problems with the prior art are to blame.

Generally speaking the relevant prior art inventions are complex, cumbersome, expensive, and risky to use (i.e. detrimental to the health of the patient). To enjoy pervasive use by the medical community, irrespective of the techniques and tools used by the artisan, the ideal system for blood glucose regulation of ICU and surgery patients must be simple and convenient to use by medical teams. The ideal system must have a low cost of ownership to the hospitals. And most importantly, the ideal system must not aggravate or compromise the health of the vulnerable patients in the OR or ICU.

One of the biggest problems with prior art automated blood sampling is clotting. To deal with the problem U.S. Patent 2007/0191716, titled Blood Monitoring System, to Goldberger et. al. has suggested the use of warfarin and heparin as an IV flush solution. Warfarin has several limitations such as it can only be given orally and not as an IV flush solution; it interacts with many commonly used medications; and frequent monitoring is required to ensure a safe dose is taken. While, natural heparin has been a commonly used anti-coagulant for IV flush solutions, its safety has been questioned for several reasons, particularly due to the potential risk of heparin induced thrombocytopenia (HIT).

A common problem plaguing the prior art is infection induced by system components and chemicals contacting re-infused blood. Pumps, valves, and sensors tend to accumulate impurities in crevices, which can contaminate bodily fluids. This is common with syringe pumps, air pumps and stop-cocks, which are typical prior art components. A typical technique for grappling with the problem is to use separate passageways for bodily fluids and medications, as in U.S. Patent Application 2006/0188407 titled Fluid handling cassette having a spectroscopic sample cell, to Gable, et al. The spectroscopic measurement method disclosed in this application requires the use of a centrifuge module that separates plasma from the blood sample for being able to perform reliable measurement. Furthermore, the system uses an extensive tubing network, and requires multiple pumps, valves and sensors, thus increasing the overall complexity and costs of producing and maintaining such systems. Another example is U.S. Patent Application 2007/0239096, titled Anti-clotting apparatus and methods for fluid handling system, to Keenan et al. This anti-clotting apparatus is restricted to a method of intermittently providing anti-clotting agents and the transmission of ultrasonic energy to a passageway of the blood flow system. The system additionally requires the use of potentially unsafe anionic detergents to clear the passageways.

Another typical problem inherent in the field is that the systems tend to draw large quantities of blood, as in the Goldberger et. al. patent. Peripheral edema is one of several complications that can ensue from drawing and reinfusing large quantities of blood. Typical prior art systems use large bore tubing, which increases the amount of blood drawn in each cycle. For example, U.S. Patent Application 2008/0097288, titled Disposable blood glucose sensor with internal pump, to Levin et al, discloses an apparatus and method for automatically and periodically measuring the level of a patient’s blood glucose when a patient has a catheter inserted in a blood vessel. The system requires the drawing and reinfusion of a large volume (2 ml) of blood for each measurement, with 200 μL being used up and the cycle having to be repeated every 60 seconds to prevent clotting. U.S. Patent Application 2008/0014601 to Goldberger et. al. suggests use of test strips based on the enzyme-glucose oxidase (GOD). GOD based strips are only suitable for measuring glucose in capillary blood derived from finger-sticks. They are not suitable for venous or arterial blood glucose measurements, due to the different oxygenation content in these blood matrices.

Another common problem in the field is controlling flush solutions with the help of gravity. Hospitals have moved away from gravity based controls, because the flow-rate cannot be precisely controlled and there is risk of excess saline being infused into the patient. Issues with accuracy of measurements and reliability of systems over protracted use plague the field. Poor sensor quality and sensor technique, as mentioned, is usually to blame. To enhance measurement accuracy U.S. Pat. No. 7,367,942, to Grage et al., requires a isolatable test chamber or side channel for the blood sample during measurement, so that there is no change in the diffusion gradient, when the blood sample is in contact with the flow-through sensor. U.S. Patent Application 2007/0225675, titled Blood Analyte Determinations, to Robinson et al, discloses methods and apparatuses to provide measurement of glucose and other analytes with a variety of sensors without many of the performance degrading problems of conventional approaches. However, as is typical of the prior art, the system requires the use of more than one pump, several valves, and a complicated tubing network. Additionally, in all prior art systems, the patient cannot be quickly and aseptically connected or disconnected from the system.

Given the state of the prior art, the present invention has various objects:

An object of the present invention is to develop a very simple but innovative system; i.e., simple and economical to make, use, and operate;

Another object is to develop a system that performs reliable automated blood sampling;

Another object is to develop a system that can operate for at least three days continuously without any human intervention when using a peripheral IV catheter;

Another object is to develop a system that effectively prevents clotting and keeps the blood passageways clear without aggravating the health of the patient;

Another object is to develop a system that has a specially designed connector to mate with the catheter hub such that the dead volume in the catheter is eliminated and the potential for thrombus formation is further minimized;

Another object is to develop a system that enables quick, aseptic connection and disconnection between the patient and the system, allowing for easy system maintenance and quick disassociation between the patient and the monitoring system for mobility;

Another object is to develop a system that utilizes a modular design such that it can be integrated with almost any kind of sensor system, including: multi-analyte flow through systems, "needle" type glucose sensors implanted in the lumen, or disposable test strips;

Another object is to develop a system that utilizes an innovative test strip feeder design and assembly that integrates with the sampling platform and allows for reliable and fully automated measurements with conventional glucose meters and test strips;

Another object is to develop a system that has a point of sampling that is not restricted to the peripheral vein, but also includes the sampling from the arterial line and central venous system;

Another object is to develop a system that is configurable to operate automatically for any length of time by the appropriate site of blood sampling, a clot-free method of sampling, micro-volume extraction of blood, and the ability to keep the veins open between sampling cycles;

Another object is to develop a blood sampling system that can also operate without the need for "reinfusion" of blood back into the patient;

Another object is to develop a system that allows a simple and reliable way to carry out therapeutic intervention based on the concentration of the blood analyte.

Therefore, in light of the foregoing, it would be further appreciated to develop a reliable blood sampling and analyzing system: simple to make, simple to use, and inexpensive to the end user; that makes use of clot-prevention techniques without compromising on the health of the patient; that uses a technique for keeping veins open during stand-by mode; that makes use of a quick aseptic connect/disconnect; that makes use of a special luer connector that mates with the catheter hub to eliminate the dead volume while also effectively reducing the chances of thrombus formation in the catheter; that employs a single blood-passageway such that the medication (insulin, dextrose, etc) and blood share the same passageway; that simplifies operations and improves overall quality of care; and that incorporates an innovative system design enabling the automated blood sampling platform to be integrated with a wide range of sensor technologies.

BRIEF SUMMARY OF THE INVENTION

The present invention is directed toward systems and methods for automatically sampling blood from a patient for analytical measurement. The present invention can be used for multiple automated diagnostic purposes, and integrated with a blood parameter monitor including a blood parameter sensor, wherein the blood parameter is selected from the group comprising: glucose, lactate, electrolytes, cholesterol, urea, and blood gases, wherein the blood parameter sensor is selected from the group comprising, a test-strip based glucose meter, an electrochemical flow-through sensor, an infrared spectroscopic flow-through sensor, and an implantable, needle-type sensor inserted in said tube set in said blood path.

In one embodiment, the present invention includes an intravenous blood access catheter for accessing said blood; a tube set that is connected to the catheter forming a single blood path for transporting and dispensing blood samples from a patient to the end of said blood path in sensing communication with an external blood parameter sensor; a saline rinse solution for priming the tube set before connecting the tube set to the catheter by rinsing the tube set with the rinse solution to remove all air bubbles eliminating the risk of air-embolism, and the rinse solution is for clearing the blood path between dispensing samples; a non-invasive air-bubble sensor and occlusion sensor to ensure the presence of fluid in the blood path and absence of any obstruction due to vein collapse or any other blockage; an in-line dilution sensor for detecting the dilution of blood in the blood path; and a single peristaltic pump and a plurality of pinch valves for controlling the flow of fluid in said blood path, for controlling dispensing samples in communication with said blood parameter sensor, for rinsing said blood path, and for re-infusing blood back into said patient; wherein said peristaltic pump and said plurality of pinch valves do not directly contact fluid in said line, eliminating the risk of contamination.

Other objects and advantages of the present invention will be readily apparent upon a reading of the following brief descriptions of the drawing figures, detailed descriptions of preferred embodiments of the invention, the appended claims and drawings.

BRIEF DESCRIPTION OF THE SEVERAL VIEWS OF THE DRAWINGS

The above mentioned and other objects and features of this invention and the manner of attaining them will become apparent, and the invention itself will be best understood by reference to the appended drawings. In the course of the following detailed description, reference will be made to the appended drawings in which.

DETAILED DESCRIPTION OF THE INVENTION

Figure 1:
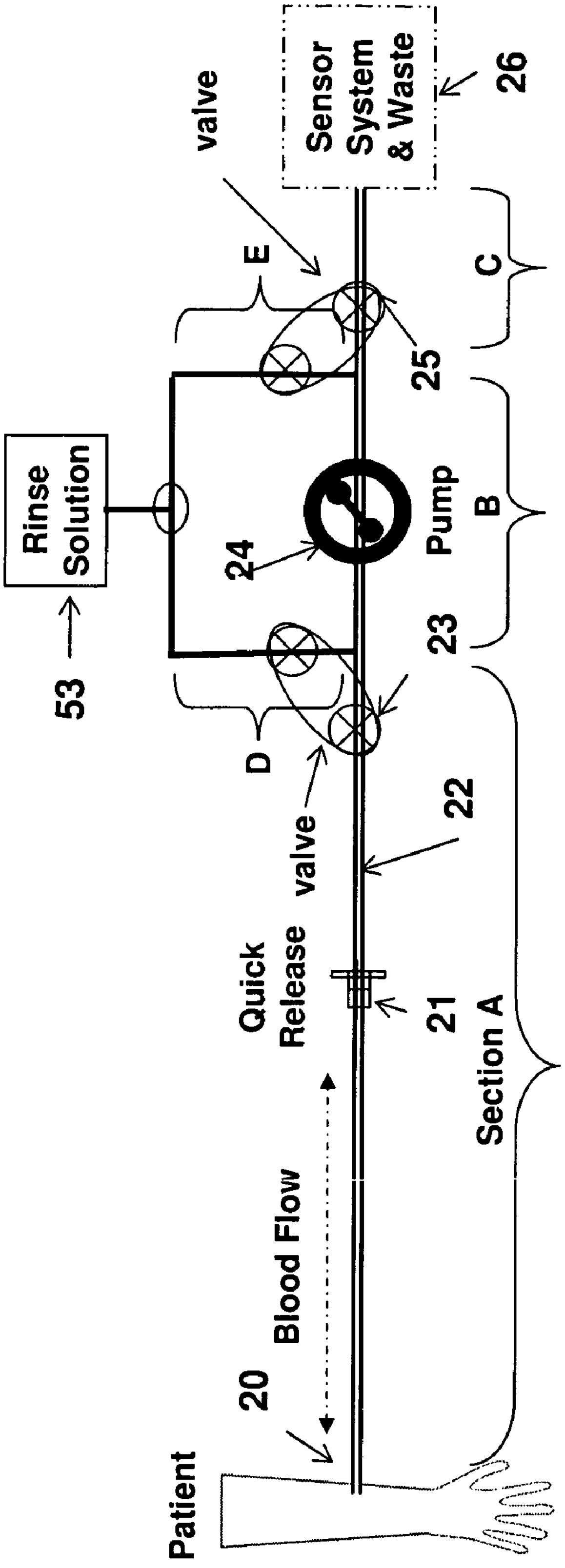
FIG. 1: Schematic of a preferred embodiment of the automated blood sampling platform

The present invention is directed toward systems and methods for automatically sampling blood from a patient. Referring to FIG. 1, a preferred embodiment of the system comprising: an intravenous blood access catheter 20 for accessing said blood; a tube-set 22 connected to the catheter 20 forming a single passageway for transporting and dispensing blood samples from a patient to the end of the passageway at a point of measurement, which is in sensing communication with an external blood parameter sensor 26; a clamp-on air-bubble sensor and occlusion sensor (not shown) externally attached to the tube set 20 near the point of sampling; two three-way pinch valves 23 and 25 spaced apart and externally attached to the tube set 20 and a single peristaltic pump 24 externally attached to the tube set 22 between said pinch valves 23 and 25; a rinse solution 53 in fluid communication with both said pinch valves 23 and 25; and a controller (not shown) operatively connected to the peristaltic pump 24 and said pinch valves 23 and 25.

Still referring to FIG. 1, the controller operates the peristaltic pump 24 in forward and reverse mode, in forward mode, when the catheter 20 is inserted in a patient's bodily fluid vessel, the peristaltic pump 24 draws blood from the patient to the point of measurement, once the blood parameter sensor 26 measures the blood sample, the controller controls the pinch valves 23 and 25, releasing rinse solution 27, rinsing said passageway; after which the controller controls the pinch valves 23 and 25 and operates the pump 24 in reverse mode, re-infusing blood back into said patient. The system can be used for multiple automated diagnostic purposes, and integrated with a blood parameter monitor including a blood parameter sensor. The blood parameter can be selected from the group consisting of, glucose, lactate, electrolytes, cholesterol, urea, and blood gases. The blood parameter sensor can be selected from the group consisting of, a test-strip, an electrochemical flow-through sensor, a mid-infrared spectroscopic flow-through sensor, and a needle-type sensor inserted in said tube set in said passageway.

Figure 4:
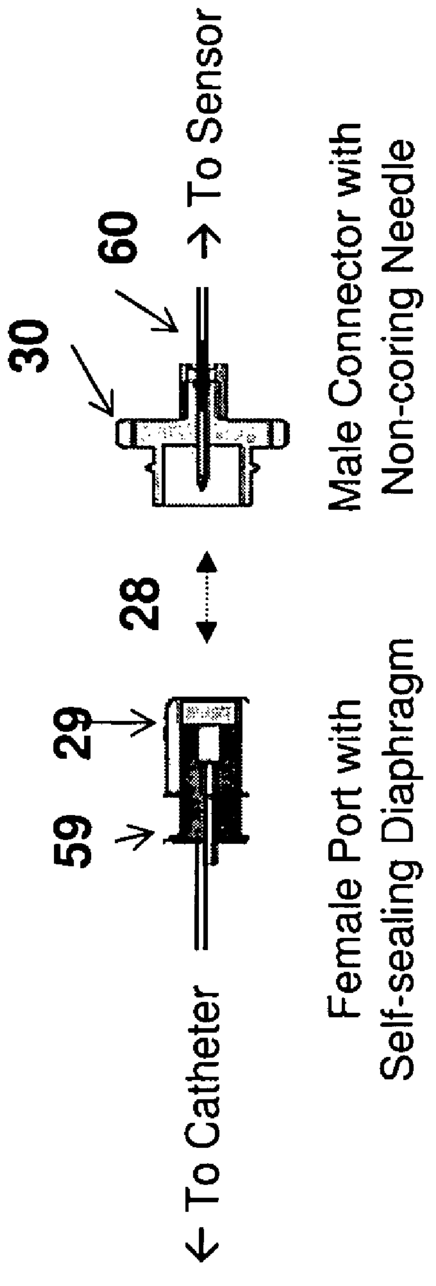
FIG. 4: Drawing of the quick aseptic connect/disconnect assembly
Figure 5A:
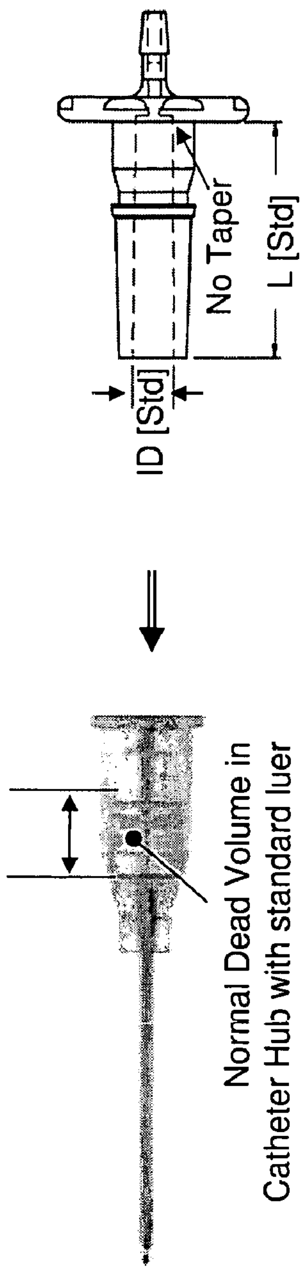
FIG. 5A: A standard male luer shown with a catheter
Figure 5B:
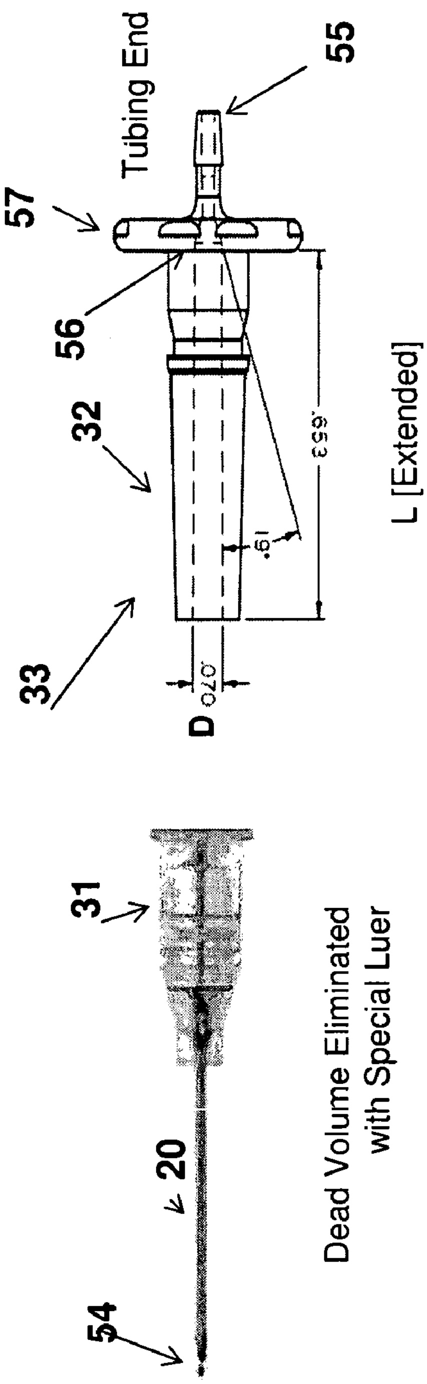
FIG. 5B: A preferred embodiment of the special male luer shown with a catheter
Figure 6A:
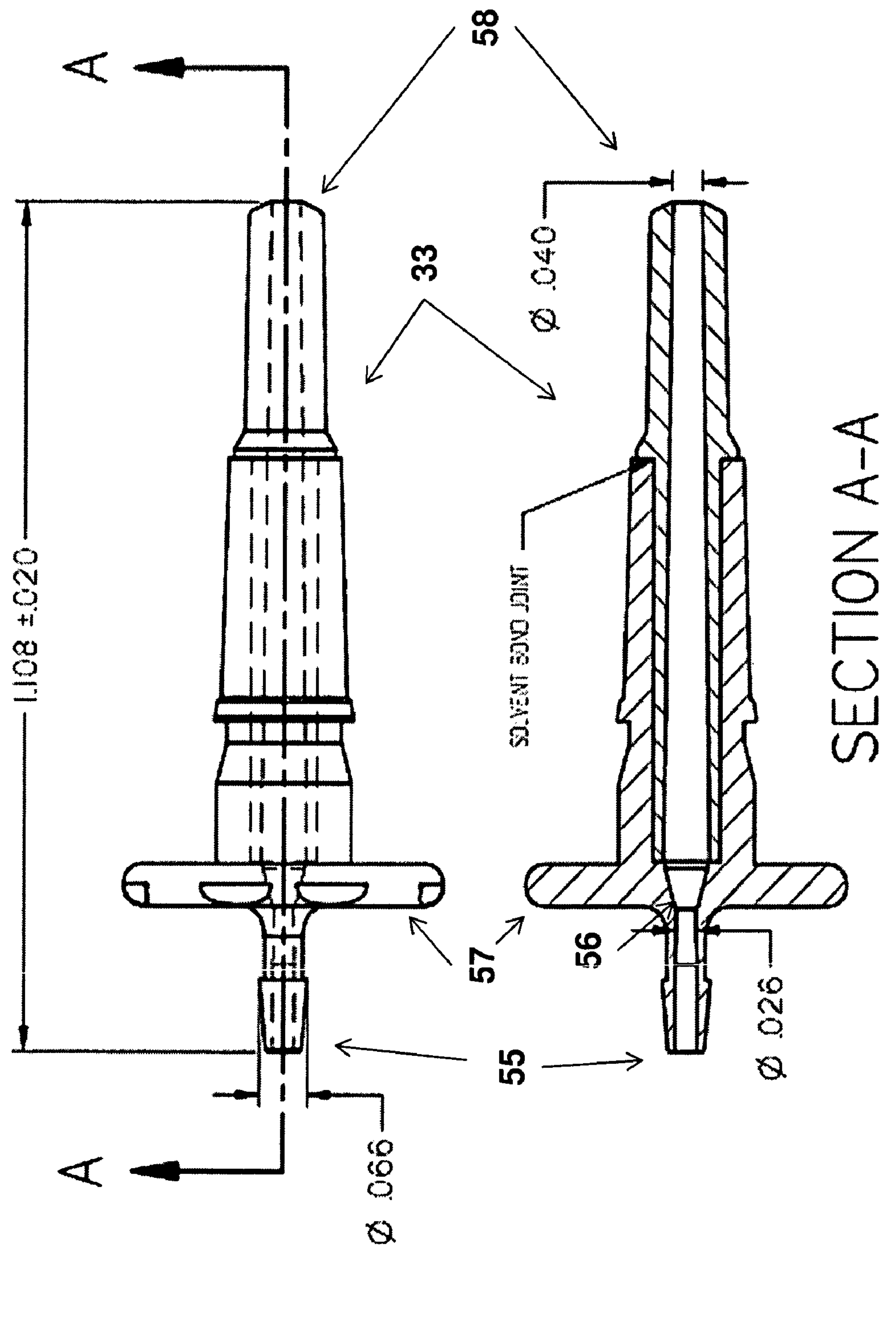
FIG. 6A: A sectional view of the special luer showing extended male section, reduced bore and tapered transition for a 22 ga catheter
Figure 6B:
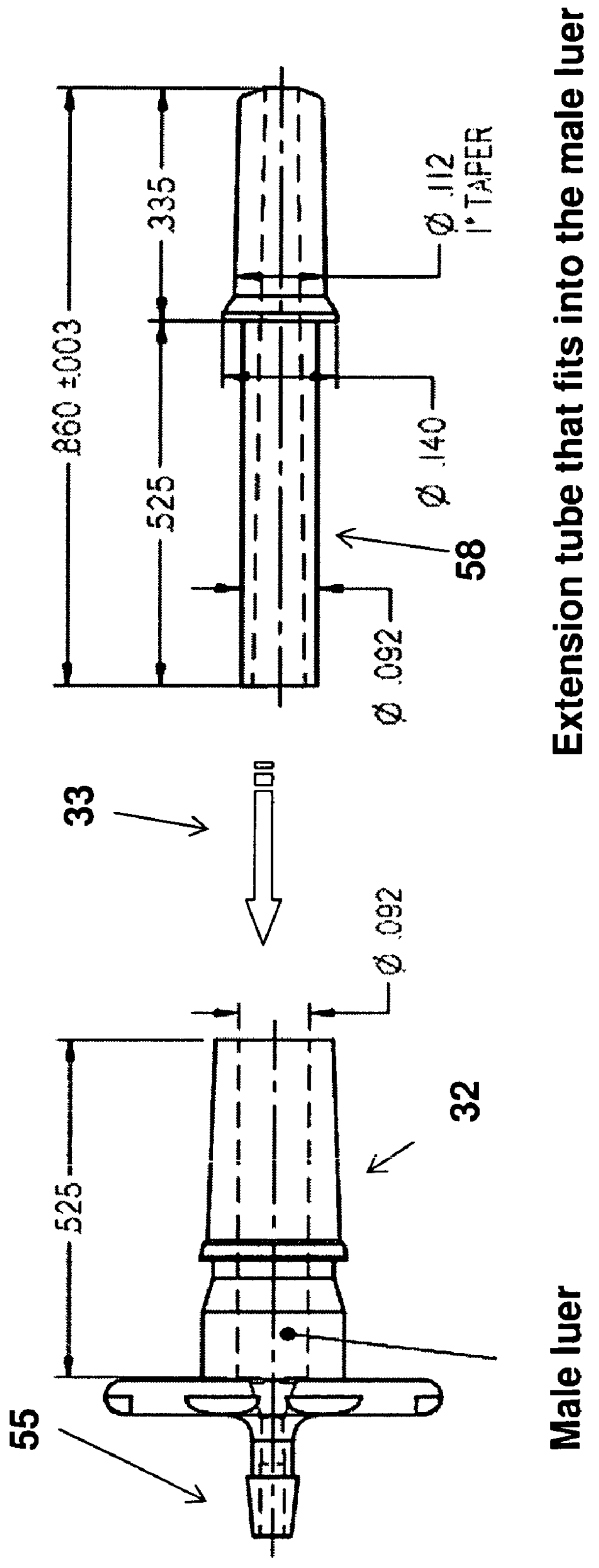
FIG. 6B: Detailed drawing of the special luer showing extended male section, reduced bore and tapered transition for a 22 ga catheter

Referring now to FIGS. 5A and B, and FIGS. 6A and B, optionally, the catheter 20 is connected to the tube-set 22 via a specially designed luer connection 33, wherein the catheter 20 comprises a patient end 54 and a hub 31 for the luer attachment; the luer connection 33 has a male end 32, a barbed end 57 spaced apart a distance L, and a cylindrical core having an inside diameter D, which is tapered at the point of transition 56 to the barbed end 57; the male luer end 32 is inserted inside the catheter hub 31; L and D are sized to eliminate the dead volume normally present when blood enters said catheter hub 31. Referring now to FIG. 4, optionally, the system includes an aseptic detachable connection 28 attached to the tube set 22 proximal to the luer connection 33, comprising a female port 29 with a self sealing diaphragm 59, a male connector 30 with a non-coring needle 60, and a leak proof negligible dead volume. Referring again to FIG. 1, optionally, a dilution sensor (not shown) can be inserted in the passageway near the point of measurement for detecting the level of dilution of blood in the blood path. Optionally, the system can be configured to draw blood and dispense samples to the point of measurement, at predefined or user defined intervals.

Figure 9:
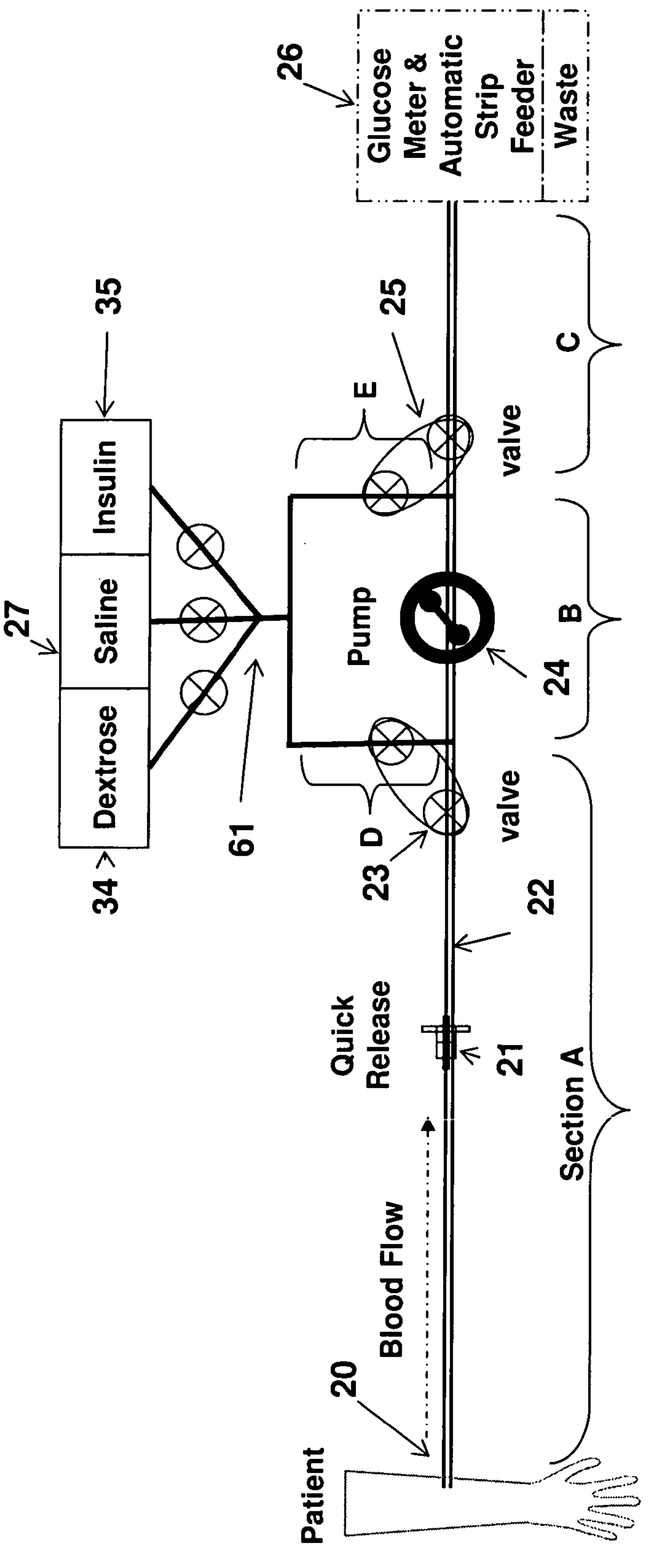
FIG. 9: A schematic of a preferred embodiment of the present invention for a test strip based automated glucose monitoring system

Now referring to FIG. 9, in a preferred embodiment, the blood parameter is blood glucose, and the blood parameter sensor 26 is a blood glucose sensor; the system includes a dextrose reservoir 34, a saline reservoir 27, an insulin reservoir 35, and a fluid selector manifold 61 interposed between the saline 27 and the two three-way valves 23 and 25, for regulating the release of the saline 27, the dextrose 34, and the insulin 35; wherein the manifold 61 defaults to saline 27, but can infuse dextrose 34, if the glucose reading is low, or infuse insulin 35, if the glucose reading is high. Optionally, the rinse solution is normal saline 27. Optionally, a small amount of anticoagulant (not shown) is added to the saline 27 selected from the group consisting of regular heparin and low-molecular weight heparin (LMWH). Optionally, the passageway is covalently bonded with heparin.

Figure 10:
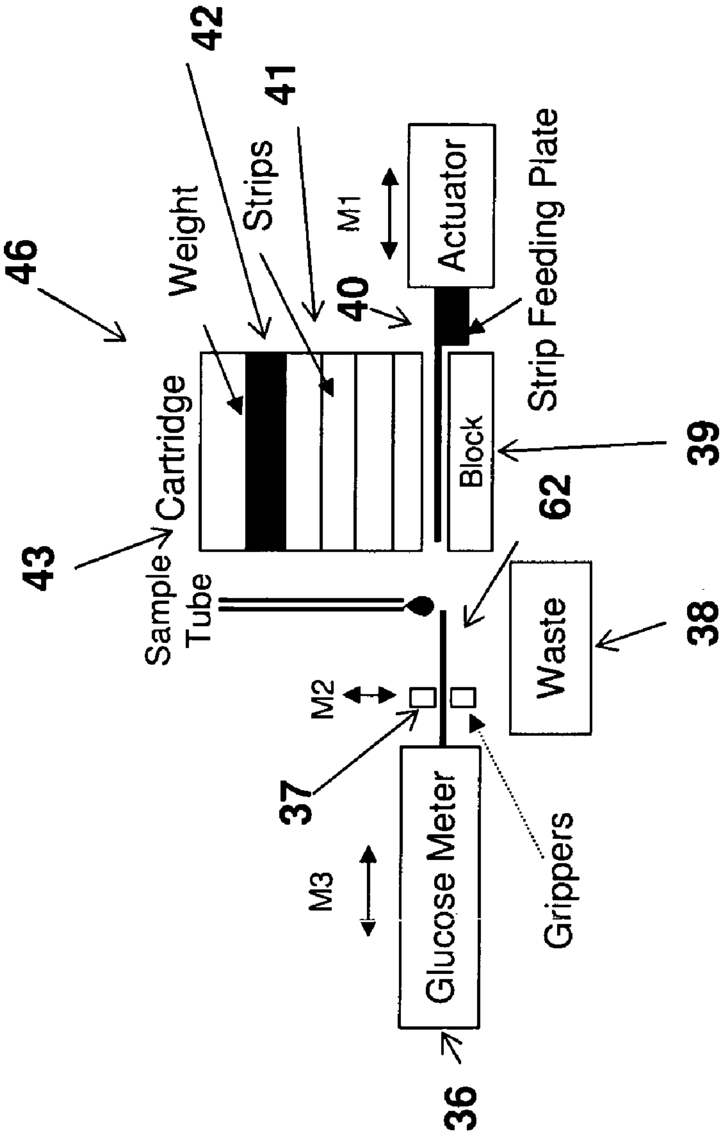
FIG. 10: A schematic of a preferred embodiment of the automated strip feeder mechanism
Figure 11A:
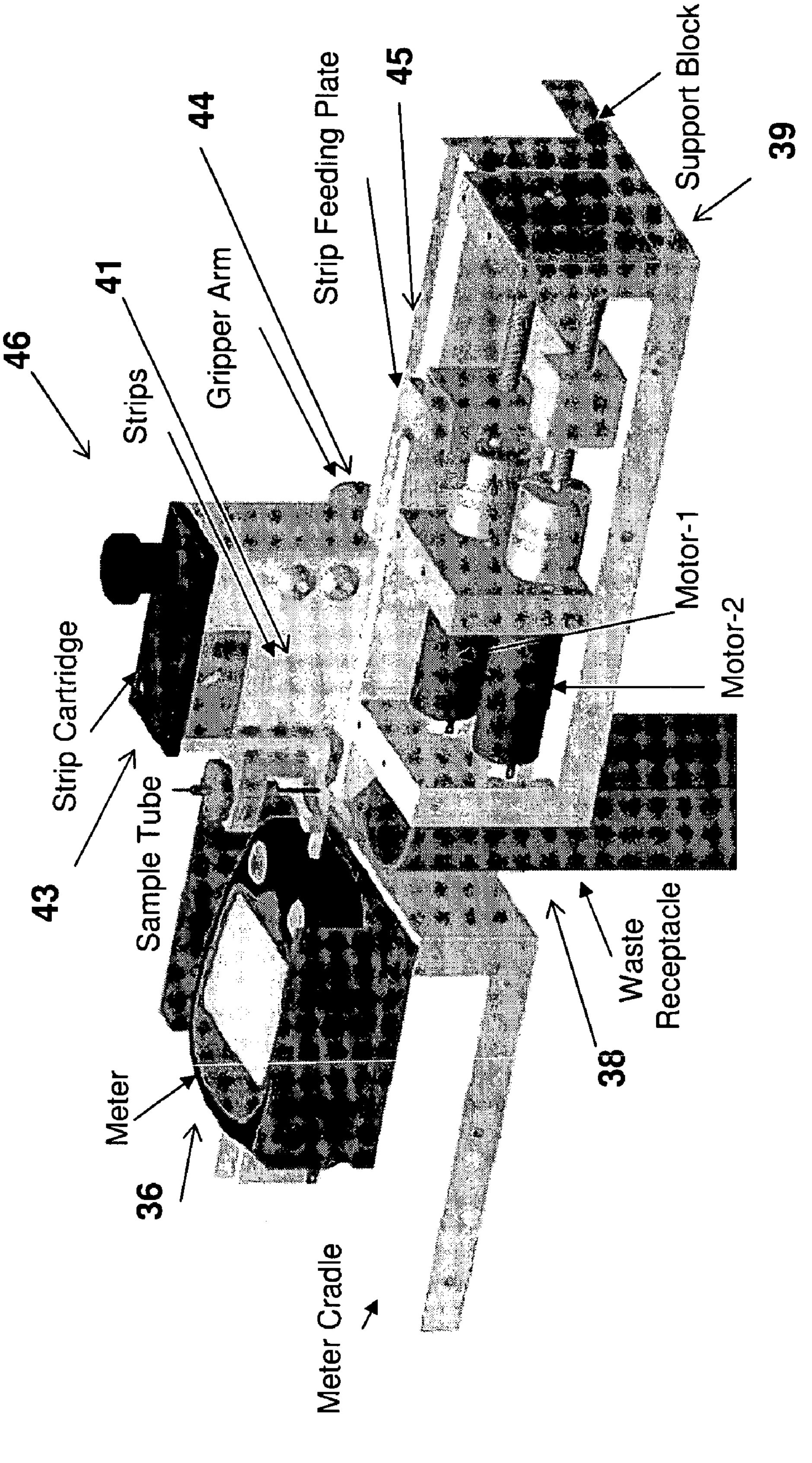
FIG. 11A: A 3-D drawing of a preferred embodiment of the strip feeding mechanism
Figure 11B:
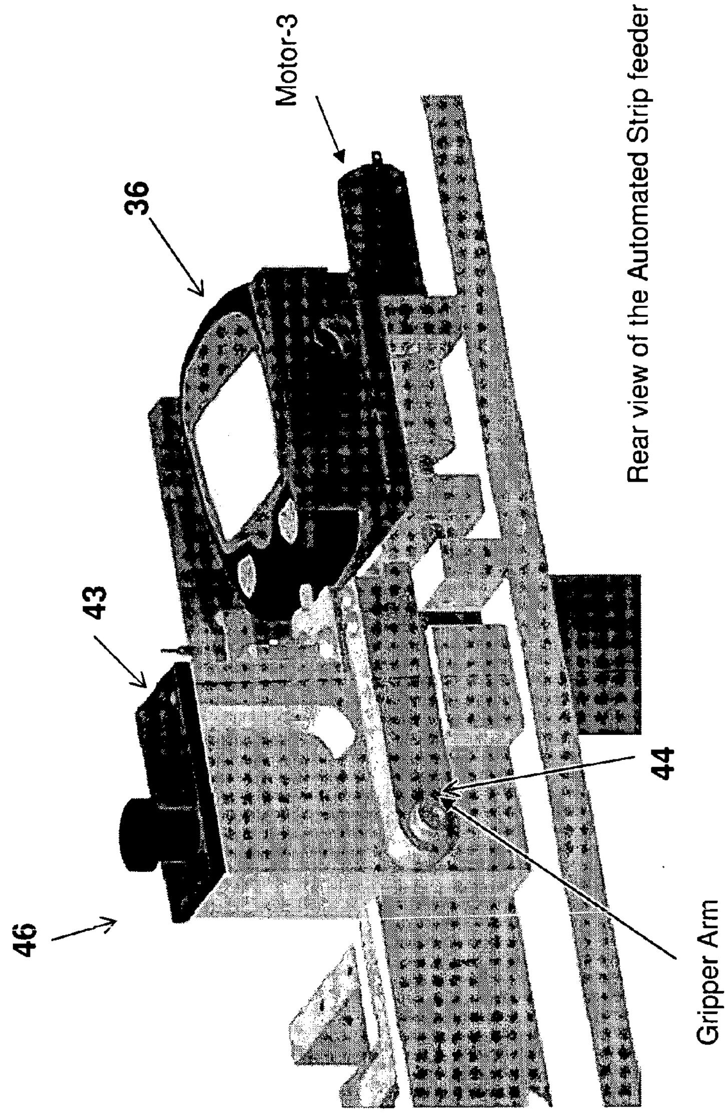
FIG. 11B: A 3-D drawing of the rear view of a preferred embodiment of the strip feeding mechanism

Referring to FIGS. 9, 10, 11A and B, in another preferred embodiment, the sampling platform is integrated with a glucose monitor in a closed loop with feedback control, the glucose monitor comprising, a test strip based glucose meter 36, a plurality of test strips 41, and means for presenting a test strip 62 in sensing communication with a blood sample at the point of measurement, and for ejecting a test strip 62 after measurement; and the system includes a waste reservoir 38 for collecting dispensed fluids and ejected test strips. Optionally, upon a user activating the system, blood is drawn from the patient and dispensed to the point of measurement, until the blood is undiluted; wherein the pump flow is reversed for a very brief period, such that any hanging blood drop is pulled back to prevent premature suction of the blood sample on a test strip 62 by capillary action at the point of measurement.

The glucose strip 62 is auto-calibrated in the meter 36, wherein the controller operates the pump 24 in forward mode dispensing a single blood sample onto the test strip 62 for measurement; then the glucose meter 36 measures the glucose concentration of the sample and displays the concentration on a patient monitor; then the blood passageway is flushed with said rinse solution; then the pump 24 reverses direction to re-infuse the unused blood back into the patient;

after the blood is re-infused into the patient the pump 24 reduces speed to slowly infuse the patient with the rinse solution just enough to keep the vein open, preventing blood clotting; during which time the system is in standby until the next predefined or user actuated measurement.

Figures 12A, 12B:
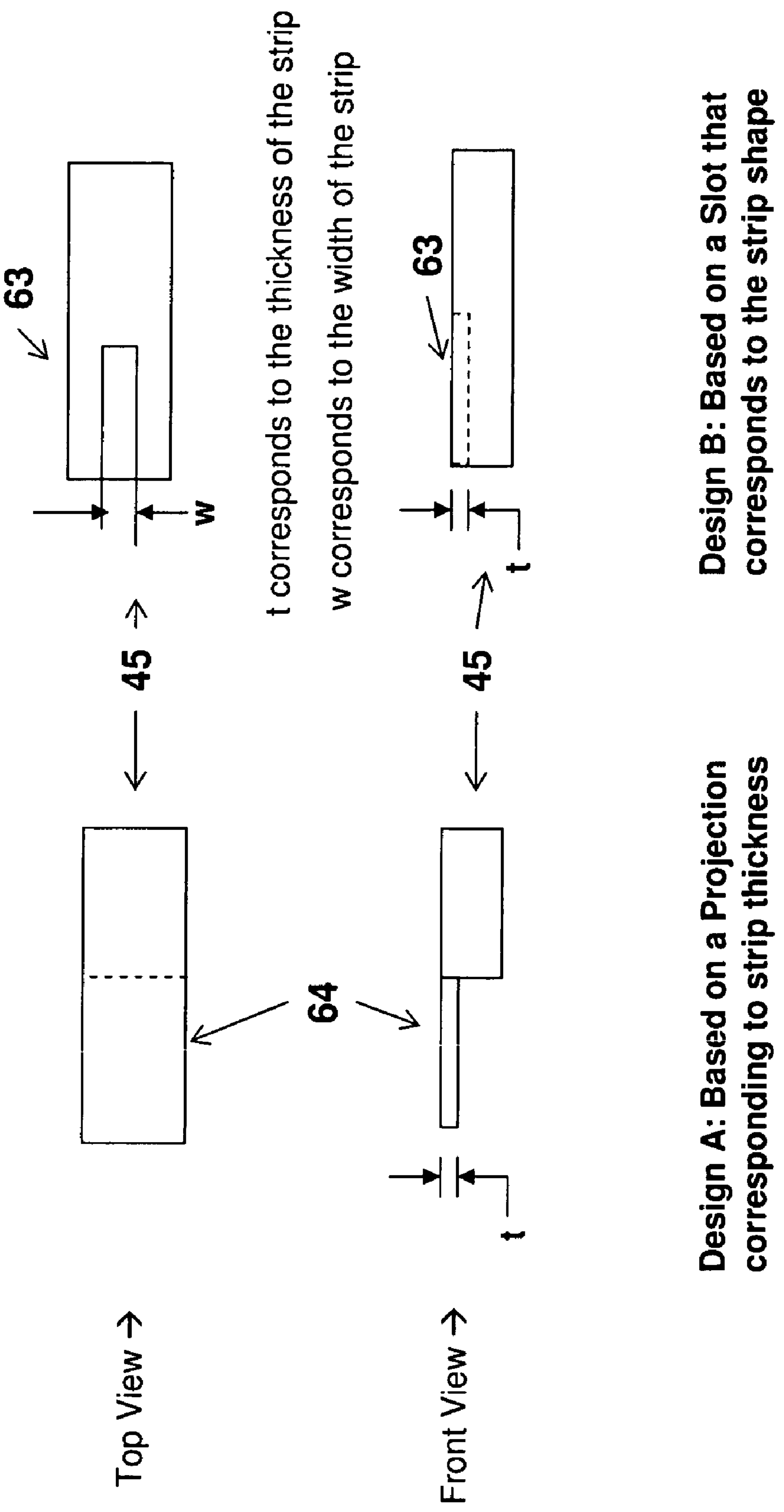
FIG. 12A: The design of the strip feeding plate based on a projection corresponding to strip thickness
FIG. 12B: The design of the strip feeding plate based on a slot that corresponds to the strip shape

Still referring to FIGS. 10, 11A and B, in a preferred embodiment, the means for presenting a test strip 62 in sensing communication with a blood sample comprises an automated strip handler 46, comprising: a resealable strip container 43 with opposed top and bottom ends, containing a plurality of strips 41 stacked there between; the container 43 is open at the bottom end, and a weight loaded at the top helps to push the strips out the bottom end; a sliding strip feeding plate 45, capable of sliding to two positions, with the feeding plate 45 having either a projection 64 to nudge the strip forward or a shape 63 etched on the top surface of the plate 45 (as in FIGS. 12A and B) to conform to accept a single test strip 62; the container 43 bottom end and the base 39 top surface are slidably attached and aligned so that a weight 42 on top pushes a test strip 62 into the slot 63 while the base 39 is in the first position; three linear feed actuators; and a gripper 37 with clamping gripper pads.

The first linear actuator slides the base 39 towards the meter 36 to the second position at the point of measurement; the second linear actuator causes the gripper pads to securely clamp the test strip 62 from the slot; the first linear actuator then slides the base 39 top surface back to position one; the third actuator then moves the meter 36 toward the test strip 62 causing the test strip 62 to be inserted into the meter 36; then the gripper pads releases the test strip 62, a blood sample is dispensed onto the test strip 62, and the meter 36 measures the glucose in the blood sample; then the third actuator causes the meter 36 to move back while the gripper pads clamps the test strip 62 thus removing the test strip 62 from the meter 36; the gripper pads releases the test strip 62, which falls into the waste reservoir 38. Optionally, the three linear feed actuators are powered by miniature motors selected from the group comprising, DC motors, stepper motors, and piezoelectric motors.

Figure 15:
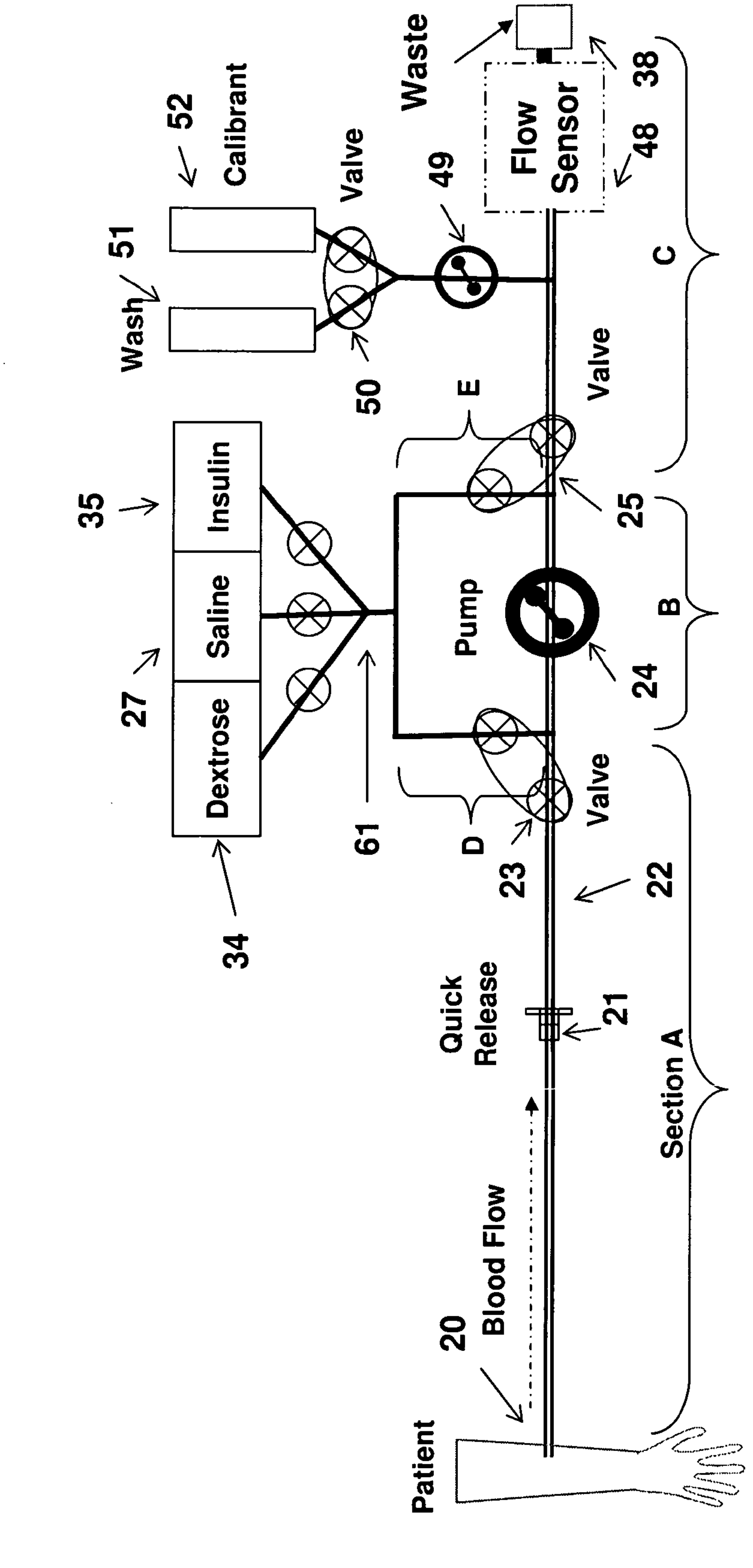
FIG. 15: Schematic of a flow-sensor based automated blood sampling and measurement system

Referring now to FIG. 15, in another embodiment of the present invention, the system comprises a flow-through sensor 48; the tube set 22 comprising an auxiliary calibration line for the flow-through sensor 48, the passageway comprising two ends, the first passageway end is connected to the catheter, the second passageway end is connected to the flow-through sensor; an in-line dilution sensor is inserted in the tube-set near the flow-through sensor; a calibrant 52 and wash solution 51 are connected to the calibration line; a third pinch valve 50 and second pump 49 are externally attached to the calibration line for regulating release of the wash solution 51 and calibrant 52; a saline reservoir 27; a dextrose reservoir 34, an insulin reservoir 35, and a fluid selector manifold 61 are in fluid communication, the manifold 61 is regulated by the first and second pinch valves 23 and 25; a controller controls the pumps 24 and 49 and valves 23, 25, and 50. When the catheter 20 is inserted in a patient's bodily fluid vessel, the controller controls the pumps 24 and 49 and valves 23, 25, and 50 to draw blood from the patient to the flow-through sensor 48, after a bodily fluid parameter is measured in the flow-through sensor 48, the controller then controls the pumps 24 and 49 and valves 23, 25, and 50, releasing rinse solution, first rinsing said passageway toward the flow-through sensor 48, then toward the patent; after which the controller controls the pumps 24 and 49 and valves 23, 25, and 50, releasing the wash solution 51, rinsing the flow-through sensor 48, then rinsing the flow-through sensor 48 with the calibrant 52.

Figure 8:
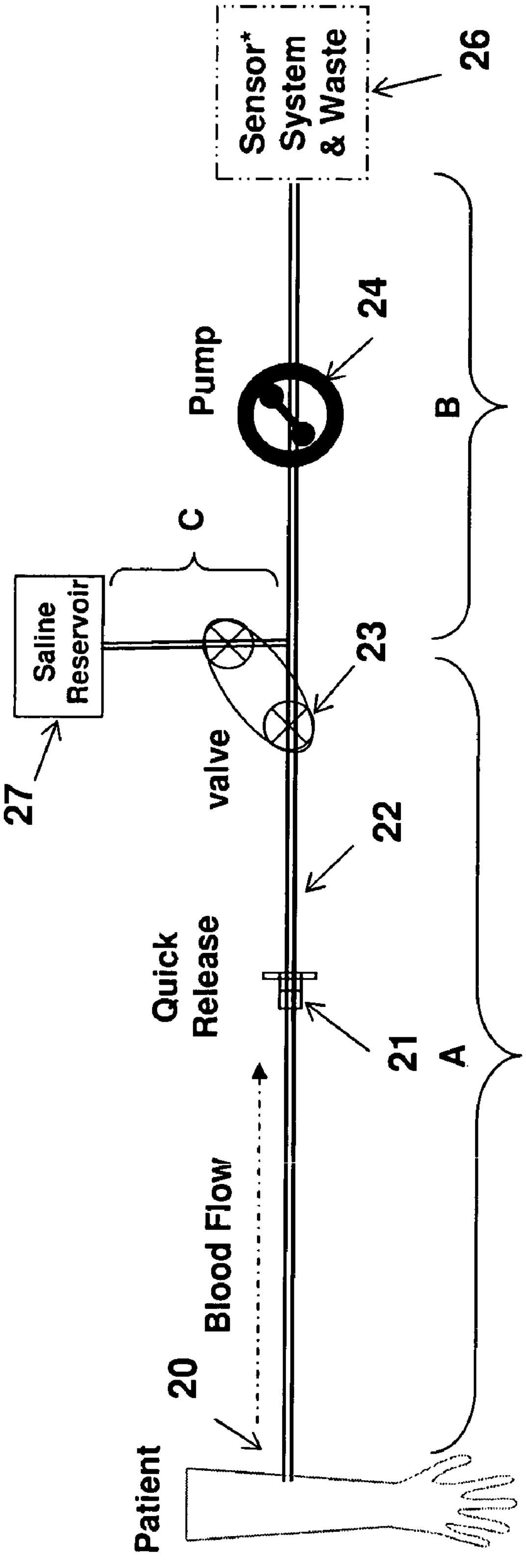
FIG. 8: A schematic of a preferred embodiment of the blood sampling platform not requiring reinfusion of blood

Referring now to FIG. 8, in another embodiment of the present invention, the system comprises: a single 3-way pinch valve 23 and a single peristaltic pump 24 externally attached to the tube set 22; the controller is configured to first operate the pump 24 and valve 23 to draw blood from the patient, dispensing a blood sample to the point of measurement; then operates the pump 24 and valve 23 to rinse said blood passageway to the waste 26.

In a common mode of operation of the present invention, the automated glucose monitoring system measures glucose near-continuously in blood drawn from a peripheral venous line. The special design of the system enables fully automated blood sampling from the patient's vein accompanied with analytical measurements. The glucose readings are displayed on the screen or the nursing station and the system also provides the capability to treat the patient in a feedback loop fashion. If glucose is out of range, the system will alert the user and suggest infusion parameters, which the caregiver will confirm or modify. The user can set various operating parameters and perform measurements on demand or automatically through an intuitive touch screen interface. The software code is written in Microsoft Visual Basic to communicate between the touch screen and the hardware control circuitry. And, the measured values are automatically shown on the screen in the form of numbers and graphs to enable therapeutic intervention.

FIG. 1 illustrates the various steps involved in a each blood sampling cycle:

1. Blood Sampling (Flow from Section A→B→C);
2. (Sensor Measurement);
3. Rinse to Waste (Flow from Section D→B→C);
4. Rinse to Patient (Flow from Section E→B→A);

The use of a single pump and two 3-way pinch valves for sampling and infusion significantly simplifies the design. However, a small "venturi" effect is observed at the tubing interconnects, causing a small slug of blood to enter the sections D and E in each cycle. To remove this small slug of blood that gets lodged in these sections, the rinsing steps 3 and 4 can be repeated after completion of all the sampling steps (1-4). The unique layout of the pump, pinch valve, and tubing in this sampling system overcomes the risk of contamination or infection to the patient from the ambient environment during sampling, measurement or infusion. A small slug of air can also be introduced by design to reduce the dilution effect while switching of dissimilar fluids (such as saline and blood) blood sampling, rinsing or sensor calibration phases. While all the figures show blood being sampled from a peripheral vein of the patient, alternate points of sampling may include the arterial and central venous lines. The peripheral line is preferred because it is less invasive and easily accessible.

Figure 2:
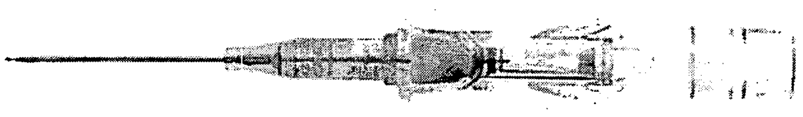
FIG. 2: A preferred IV catheter—the BD Insyte Autoguard Shielded IV Catheter
Figure 3:
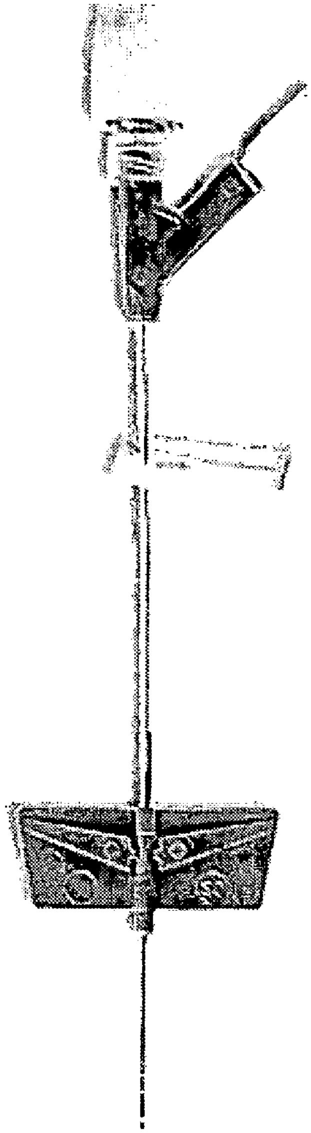
FIG. 3: A preferred IV catheter with Y-adapter—the BD Saf-T-Intima Closed IV Catheter

The peripheral IV catheter to use for best results is the 22-gauge BD Insyte™ Autoguard shielded IV catheter, FIG. 2, with Vialon™ material (BD Medical, UT). The advantage of using the BD Vialon™ is that it has high kink resistance and reduced risk of mechanical phlebitis compared to traditional catheters made up of FEP polymer. Alternatively, another suitable IV catheter is the 22-gauge BD Saf-T-Intima™ with Vialon™. The Saf-T-Intima™ catheter, FIG. 3, has the advantage of an integrated Y-adapter. This adapter provides a convenient way to manually pre-prime and flush the catheter with a syringe, if needed. In general, larger catheter bore sizes (20 ga and larger), while being more invasive, will work almost as well as the 22 ga catheters with smaller bores (i.e. 24 ga and smaller); smaller catheter bore sizes are prone to getting clogged with the red blood cells.

For best results, the entire tube set should be made of medical grade material (such as Silicone or C-flex) and have an internal diameter (ID) of 0.50 mm (0.02 inch). Although, Silicone enjoys widespread use in medical applications it has higher gas permeability than C-flex. However, unlike C-flex, Silicone can withstand steam autoclave. Smaller bore of 0.38 mm (0.015") will also work well. Larger ID tubing obviously increases the blood volume required to be transported. The 0.5 mm ID tubing translates to a tubing volume of merely 2 μL/cm. This results in the length of each of various sections of the tubing being less than 10 cm. The length of the tubing that connects to the catheter, in this case, would range from 30 cm (1 ft) to 120 cm (4 ft). For best results, the micro-flow peristaltic pump (Instech Labs, PA) should be operated at flow-rates ranging from 10 μL/min to 1000 μL/min. In the past these particular pumps have been restricted to animal blood sampling/infusion studies.

For best results, the special quick aseptic connect/disconnect device is used for rapid connection and disconnection of the tubing that connects the patient and the monitoring system as and when needed. Referring to FIG. 4, this unique assembly consists of 2 parts, namely a female port 29 with a self-sealing diaphragm 59 and a male connector 30 with a non-coring needle 60. The female port connects to the catheter while the male connector connects to the monitoring system. The tubing on either end preferably has an ID of 0.5 mm. The male connector can also be used for manual flushing of the line with a syringe. Thus far, such connections were restricted for use as part of a vascular access harness (Instech Solomon, PA) involving studies with small animals.

The intermittent normal saline (i.e. 0.9% sodium chloride solution) infusion maintains catheter patency and keeps the passageways clear. For this technique to work effectively, a specially designed luer connector is used, such that it mates with the catheter hub in an air-tight fashion while also eliminating the dead volume in the hub. The custom design features of this special luer are: longitudinal extension of the male luer end into the catheter hub, reduction in the bore of the luer extension, and provision of a taper at the point of transition to the barbed end. FIGS. 5A and B illustrate this technique of the special luer male luer by contrasting it to a standard male luer. The dead volume in the catheter hub associated with the use of a standard luer is also highlighted. It may be noted here that this combination of the catheter and luer by itself can be used independently as part of a zero-dead volume manual blood sampler. This minimizes the large blood waste (~5 ml) that occurs in current manual blood sampling methods. The material of choice for this custom luer from sterilization standpoint would be polycarbonate. This material is transparent and can also be steam autoclaved as opposed to requiring radiation or ethylene oxide sterilization. The detailed drawing of this custom luer along with dimensions is shown in FIGS. 6A and B. It may be noted here that the design of this innovative luer is based on a simple two part assembly for easy manufacturability. The male luer shown will also require the use of a corresponding stationery lock ring (not shown) to provide a secure air-tight fit. The advantage of using the special luer connector is that doing so eliminates any stagnant (dead) volume of blood in the hub, while also avoiding clot formation in the catheter. Thus with this special luer, the blood sampling system can work reliably with just normal saline infusions (i.e. without the need for using heparin).

It is highly preferred to use normal saline as stated above given the simplicity of this approach. However, one may add a very small amount of heparin flush lock solution to the saline bag to further reduce chances of blood clot formation in the catheter or tubing. As an example, a standard 10 ml vial (10 USP units/ml) of the heparin solution is added to the 100 ml saline bag thus producing a low-dose heparinized saline solution. It may further be noted here that heparin in its natural (i.e. unfractionated) form has an average molecular weight of about 20000 Da and is still used as an anticoagulant. There however is a low-molecular-weight heparin (LMWH) class with an average molecular weight of 3000 Da and a much smaller risk of heparin-induced thrombocytopenia (the most feared potential side-effect of natural heparin). Although LMWH has not been indicated for use as an IV flush solution, the inventors have discovered that when LMWH is pre-mixed into the saline bag, the mixture can prevent thrombus formation in the line, while minimizing the risk associated with natural heparin. Alternatively, another unknown technique is that heparin may also be covalently bonded to the entire blood contacting fluid passageway to obviate the need for any heparinization of the saline bag.

Non-contact sensors along the tube-set are helpful to alert the user with any operational problems. The most important ones include: air-in-line detection and occlusion detection. The clamp-on air-in-line sensor (Introtek, NY) is based on ultrasonic technology and alerts the user of any potential flow obstruction or leakage, which usually manifests itself in the form of air-bubbles. The air-in-line sensor with different sensitivity settings will alert the patient and clinician if air is present in the tube-set. The occlusion sensors (SMD Sensors, CT) installed upstream and/or downstream will alert the patient and clinician if interruption of fluid withdrawal or infusion occurs. These "tube sensors" are based on thin film technology that monitor pressure by measuring the force exerted onto a sensor by the pressure in disposal-set tubing. In use, the sensor is mounted into a housing, which is clamped onto the tube. The load-button of the detector presses against the tube wall such that expansion in the tube due to pressure changes is measured by the sensor. The resulting signal is proportional to the pressure, if the correct pre-compression is applied to the tube. Silicone tubing gives best results from this approach, as it has low creep over time. One may also optionally use an inline dilution detector (based on hematocrit measurement) near the point of sensor measurement. This will help to make sure that the blood sample reaching the sensor is not diluted. Note that the hematocrit measurement principle is based on making impedance measurements and the blood that comes in contact with the dilution sensor is not re-infused back into the patient. This inline hematocrit sensor may also be used to mathematically correct the inaccuracies associated with high and low hematocrit values that are not uncommon in critical care settings. External sensors may also be used to detect the presence of fluid in the tubing or the waste container as well.

Figure 7:
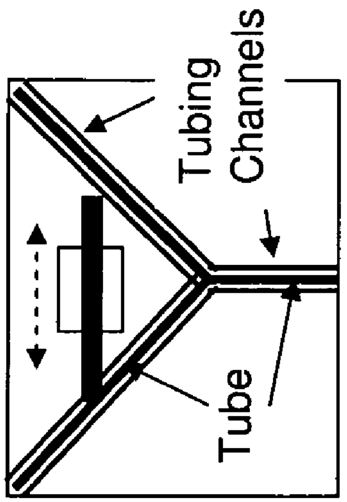
FIG. 7: A schematic of a preferred embodiment of a piezo-electric micro-motor based pinch valve

It is preferable to use pinch valves, which allow the blood in the tubing to be mechanically and electrically isolated. The pinch valves work by pinching the tubes thus preventing fluid flow in a given direction. The pinch valve is usually actuated by solenoids. However solenoids draw a lot of power and make it unsuitable for battery operation. For best results one can use piezoelectric linear micro-motors which are both low power consuming and highly miniaturized. Tube pinching in this novel design would be achieved by placing the tube in a channel and providing an access to the piezo motor shaft for reciprocal movement (FIG. 7). A possible supplier of piezo-motors is Newscale Technologies, NY under the registered name of "squiggle" motors.

The present invention is also directed at a blood sampling system that functions without re-infusing the blood back into the patient. For best results the blood contacting surfaces should be coated with heparin, to prevent clotting in the portion of the blood that stays stationary in the catheter. During the heparin coating or immobilization process, it is desirable to maintain the functional activity of heparin. Common coating methods include, ionic bonding, use of heparin complexes and covalent cross-linking. The end-point covalently bonded CBAS™ (Carmeda Bioactive Surface) is a preferred coating option as it is non-leaching. Alternative anti-thrombogenic coatings may include those based on TDMAC Heparin (Polysciences, PA) or BioLast™ (AST Products, MA). These coating types may also be used to offer hydrophilic and lubricious property to the tubing. FIG. 8 shows a schematic of an embodiment of the blood sampling platform without a blood re-infusion cycle. The various steps involved in each blood sampling cycle are as follows:

1. Blood Sampling (Flow from Section A→B);
2. (Sensor Measurement);
3. Rinse to Waste (Flow from Section C→B).

Thus blood in section A is not reinfused into the patent. The advantage of this embodiment is that the system is simpler in construction (only one 3-way pinch valve), operation (fewer steps and no reverse flow of the pump) and arguably safer than the earlier mode which involved blood re-infusion. However, the drawback is a relatively larger (dead) volume which needs to be discarded for each measurement. This will be particularly pronounced when sampling blood from the central venous system, since the latter requires relatively long catheter tubing that dwells inside the patient.

Using any of the blood sampling platform embodiments illustrated herein, the sensor system to be integrated can be in the form of single use test strips or multi-use flow-through sensors. In the case of strips, an automatic strip feeder mechanism can be used to present the strip for measurement at the appropriate time; whereas using a flow sensor would form a closed system requiring an automated calibration sequence. Both of these approaches are now described assuming the blood re-infusion mode. The non re-infusion mode is a more simplified version of these approaches, as described earlier.

With the test-strip-based approach, glucose measurements are automatically performed by dispensing blood on to a standard test-strip based glucose meter that is integrated with the sampling unit. The system automatically samples blood from a patient's peripheral vein for measurement at user defined frequency. The automated strip feeder presents the strip for accepting the blood sample for measurement in the meter followed by discarding the strip. The blood sampling platform remains the same as described earlier. The 3-way pinch valves direct fluids along different sections and a fluid selector manifold provides the capability for infusing dextrose or insulin (as the case may be) through the same tube-set and catheter connection. FIG. 9 shows the schematic of an embodiment of the strip-based approach.

Under a preferred mode of operation, the first step is to prime the patient-dedicated tubing, which fills the entire tubing with saline. This removes all air bubbles before connecting the system to the catheter for blood sampling. Blood only comes in contact with the sterile tube-set and the use of pinch valves electrically isolates the device from the patient. Thereafter the sequence of steps is as follows:

1. Pre-sample: Gets venous blood to the end of the dispensing tube until blood is undiluted;
2. Short Reverse flow: Any hanging blood droplet is pulled back into the tubing. This prevents untimely sample suction of a blood drop by the strip. Meters give an error if the sample is applied too soon onto the strip;
3. Present Strip: the automatic strip feeder mechanism presents a test-strip for measurement by inserting it into the meter;
4. Dispense sample: the pump dispenses a blood drop onto the strip for measurement;
5. Wait Time: The glucose meter performs the measurement;
6. Glucose reading: The glucose meter displays the concentration and the reading is transmitted to a monitor using the communications protocol;
7. Eject strip: The automatic strip feeder grabs the strip and removes it out of the meter;
8. Wash/Rinse waste: Flow saline to clear the end tubing section;
9. Re-Infuse/Flush patient: Reverse pump direction to re-infuse the unused blood back into the patient;
10. Optional Advanced Rinse Mode: Slow saline infusion to keep vein open, before the next measurement;
11. Stand-by: This is the wait period before starting the next measurement during which therapeutic infusions may be done;
12. Repeat above steps at the user defined frequency of measurement.

Not all test strip chemistries are suitable for working with venous or arterial blood. Most commercially available strips are based on measuring glucose in capillary blood derived from finger sticks. Capillary blood has different level of oxygenation compared to venous or arterial blood. In light of the above, strips that are based on the enzyme glucose oxidase (GOD) are not appropriate for vascular derived blood samples, since the enzymatic reaction is oxygen dependent. Test strips based on the enzyme glucose dehydrogenase (GDH) work best because the enzymatic reaction is oxygen independent. Other critical factors to consider for strip selection include the ability to accurately detect glucose under low and high hematocrit levels as well as have minimal bias associated with endogenous and exogenous interferents. Such potential interferents that may be present in the blood of critically ill patients include cholesterol, bilirubin, urea, ascorbic acid, acetaminophen, maltose, galactose, etc. It may also be noted here that glucose dehydrogenase generally uses one of three cofactor enzymes for the enzymatic reaction to take place. These co-factors (in their abbreviated form) are PQQ, FAD and NAD. Of these PQQ has an interference issue with maltose and galactose, while FAD and NAD do not. The currently well known examples of GDH-FAD/NAD based test strips include: Ascensia Contour (Bayer Healthcare, IN), Precision (Abbott Labs, IL), Statstrip (Nova Biomedical, MA), and Glucodr (All Medicus, Korea). Among these, the potential bias due to extreme concentrations of hematocrit is the least with strips of Contour and Statstrip.

The strip feeder mechanism automates the process of taking a strip from a container followed by inserting the strip into the meter for blood application and finally ejecting the strip out of the meter for waste disposal. The automated strip feeder (ASF) uses three motorized actuators that perform the necessary steps. In a preferred embodiment, there are 3 linear motors (one each for linear movement of the strip feeding plate, strip support block/gripper and the meter respectively), a strip gripping mechanism, and a resealable strip holder containing several glucose test-strips. The strip holding container minimizes the effect of ambient humidity, which may affect the strip chemistry. A schematic of a preferred embodiment of the strip feeding mechanism is shown in FIG. 10. 3-D drawings of a preferred embodiment of the strip feeder module is shown in FIGS. 11A and B.

Figure 13:
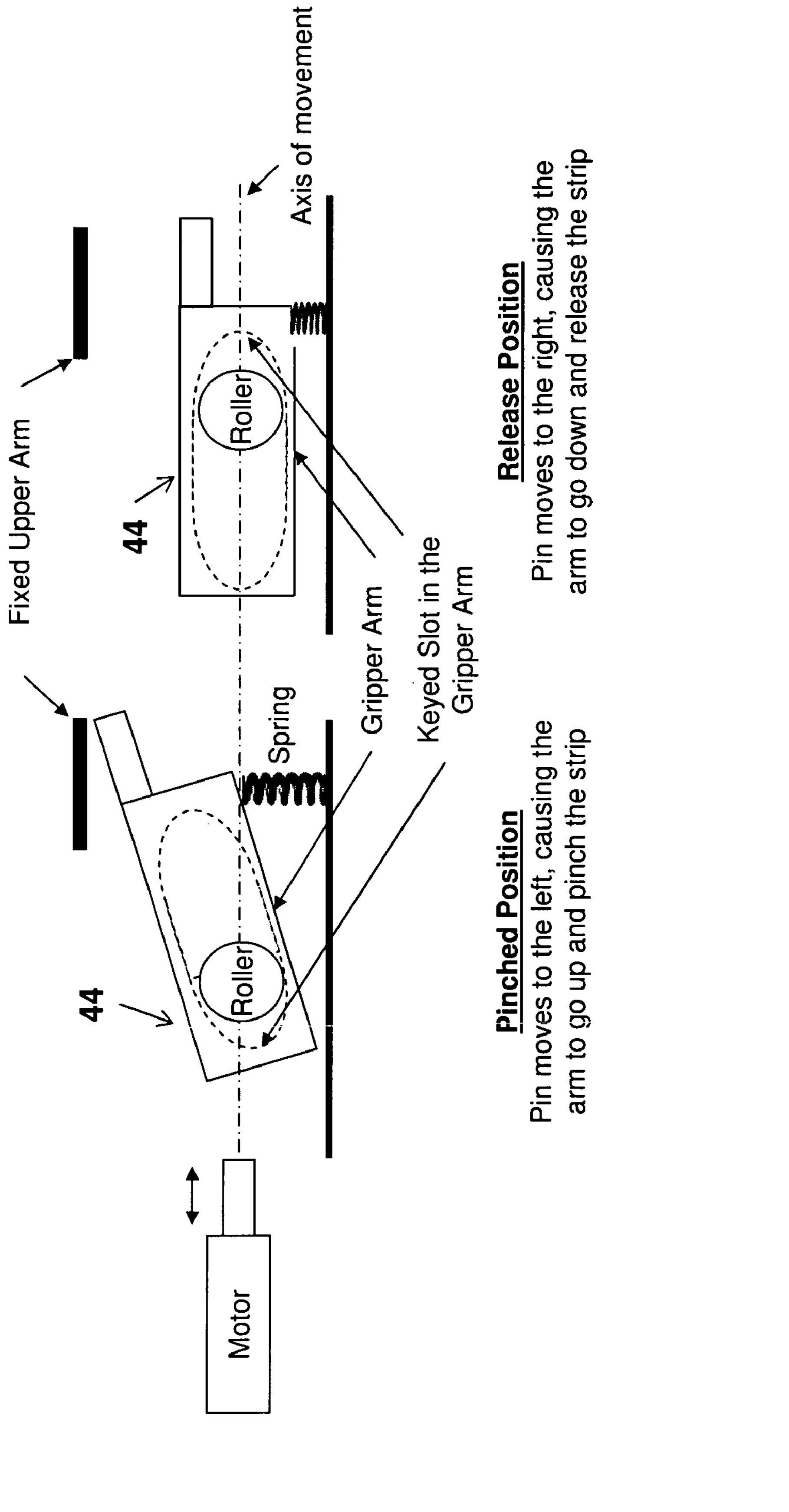
FIG. 13: Detailed schematic of the motorized "strip" gripping mechanism
Figure 14:
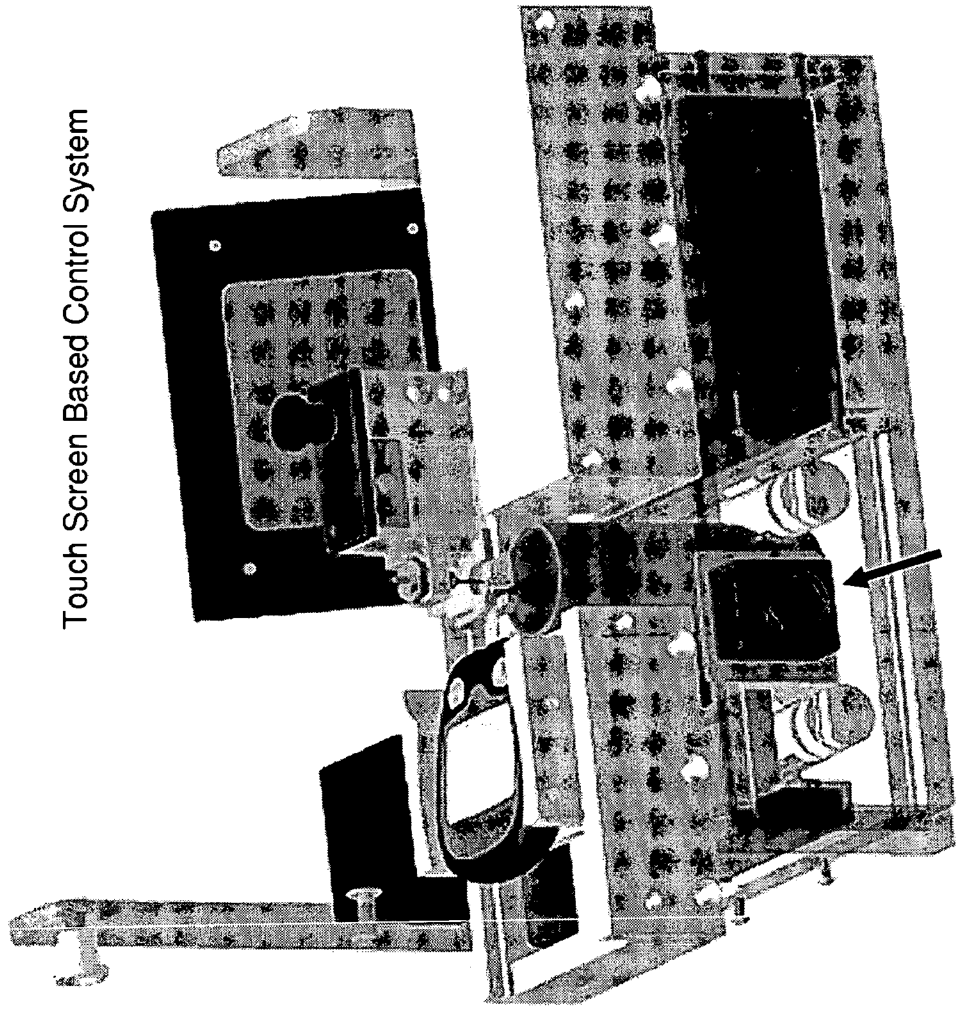
FIG. 14: Complete assembly of the test-strip based automated monitoring system with the main modules

The strip container is open at the bottom to fall into the strip feeding plate. A linear actuator (M1) moves the strip feeding plate forward, with the plate fabricated such that there is either a projection on the plate corresponding to the thickness of the plate or the top of the plate surface is etched such that it conforms to the shape of the test strip. Both of these designs have been shown in FIGS. 12A and B. The second motor (M2) operates the gripper mechanism. The gripping action is made possible by converting the horizontal movement of the support block by M2 to vertical movement of the gripper arm. This is illustrated in FIG. 13. As shown in the figure, the support block moves forward with motor (M2), a roller pin within the keyed slot of the gripper arm causes the arm to move up or down producing the gripping and release actions. A coiled spring causes the gripper arm to return to its default position. In the pinched position, the roller pin moves to one end, causing the arm to go up and pinch the strip, and in the release position, the roller pin moves to the right, causing the arm to go down and release the strip. The support block has two functions. The first is to provide a supporting base for the strip when it moves out of the cartridge containing the strips until it goes into the meter and the second function is to enable the gripping action. Once the gripper arm secures the strip in its place, the other linear actuator (M3) will move the meter to have the strip inserted. Once the strip is properly inserted into the meter the gripper arm releases the test strip and the blood sample is dispensed on to the strip. The glucose is measured and displayed on the meter and also automatically transmitted to a computer monitor through a data cable or by wireless means. The gripper arm then secures the strip again as the strip is ejected by the retraction of the meter. The grip is then released for the strip to fall into the waste container. The size of the gripper pads is small and the point of gripping on the strip is such that it is not in the middle of the strip. This causes the unbalanced strip to easily fall in the waste by the effect of gravity. The fluidic rinse cycle is then completed and the above steps are repeated as before. FIG. 14 shows integrated assembly of the strip feeding module with the automated blood sampling system.

The risk of contamination is eliminated by not letting the fluid in the sterile tube come in direct contact with non-sterile surfaces like test-strips. It is known that no risk of infection is posed to the patient by mere air exposure of blood at the end of the tube. Safe handling and disposal of the blood and saline waste is achieved through the use of a spring loaded cap on the reservoir and a tilt sensor to automatically close the cap in case of tripping. The strips are stacked and held firmly in a cartridge. The automatic strip feeder (ASF) mechanism can hold dozens of strips. For example, a cartridge storing 50 strips enables the ASF to operate without a refill for at least 12 hours, assuming measurements as frequent as every 15 minutes. The testing frequency is usually reduced as the glucose in the patient becomes stabilized. The strip loading is made easy by pre-assembly of 50 strips during manufacture. The ASF interfaces with an OEM type glucose meter and the timing is controlled by the embedded controller software. The glucose measurement values can be transmitted and displayed on a patient monitor in real-time using the appropriate data communications protocol. With most meters, the meter turns on when the strip is inserted and turns off when the strip is ejected. Furthermore, the data communication between the meter and the computer requires manually connecting the data cable and activating the appropriate software. Additionally some meters do not allow for glucose measurements when the cable connection is in place. The cable needs to be manually removed to allow for measurement. A similar logic applies for wireless communications protocol. Clearly, such manual processes are an impediment in the path towards fully automated monitoring.

The present invention addresses this problem by employing a method that enables automated measurements by replacing the cumbersome manual processes of data communication. One of the ways to overcome this problem is by installing an electrical relay in the cable that is periodically switched on and off by the system controller during the download and measurement phases respectively. In cases where the glucose meters require the pressing of a button on the meter to enable data download, appropriate electrical solenoids can be used in lieu of any manual pressing operation. The downloaded glucose values can then be appropriately graphed and/or numerically displayed on the monitor and alert the user when the readings are out of the safe zone. Thus the system eliminates the manual processes that involve connecting or disconnecting the cable and or pressing of various keys on the meter to perform glucose measurements or read the glucose values.

While this automated strip feeder (ASF) embodiment is applicable for the common case where the strips are stacked one over the other; the ASF works equally as well for the cases where strips are packaged in a drum or in a disc that is popped into and out of the meter. In such cases, the only motorized actuation required would be the operation of the strip presentation/ejection button(s) present on the meter. Further, it should be noted here that the automatic strip feeder mechanism is not just restricted to glucose test strips, but the term is also intended to include other single use test sensor elements in the form of cartridges and cuvettes that are used for handheld glucose or other blood analyte measurement. An example of a cartridge based system is the I-Stat (Abbott Point of Care, NJ); that for a cuvette based system is the Hemocue 201 Analyzer (Hemocue Inc., CA).

Figure 16:
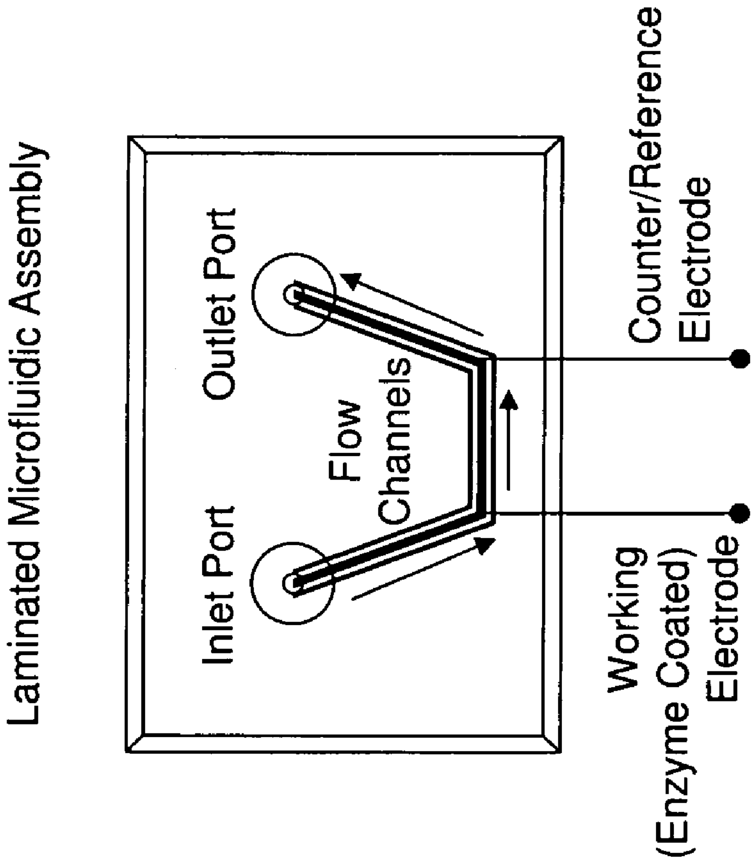
FIG. 16: A 2-electrode flow-through glucose sensor design

The flow-through sensor approach will now be described. The blood sampling platform remains unchanged as before, except that in place of the test strip; a flow-through sensor system is used. An additional pinch valve and a pump are used to allow for automated sensor calibration. The flow sensor has an electrical interface that produces a signal proportional to the glucose concentration. FIG. 16 shows a simple yet innovative design of a 2-electrode flow-through glucose sensor made by plastic lamination technology. One end of the working electrode has the appropriate enzyme immobilized by one of several known techniques. The leads of the electrodes are connected to a potentiostat for quantification of analytes like glucose. The flow-sensing system is primed with saline as always before connecting the system to the patient. The system performs a two-point calibration prior to the start of the measurement cycle. Blood is sampled from IV catheter and is transported to the flow-sensor and then to the waste. Glucose (or any other analyte) is determined electrochemically. The sequence of system operation is as follows (FIG. 15):

1. Draw blood from patient to sensor;
2. Measure the blood analyte in the flow sensor;
3. Rinse the line to the sensor using saline;
4. Rinse the line to the patient using saline;
5. Wash the sensor using wash solution;
6. Calibrate the sensor using calibrant;
7. Repeat above steps at user-defined time intervals.

Figure 17:
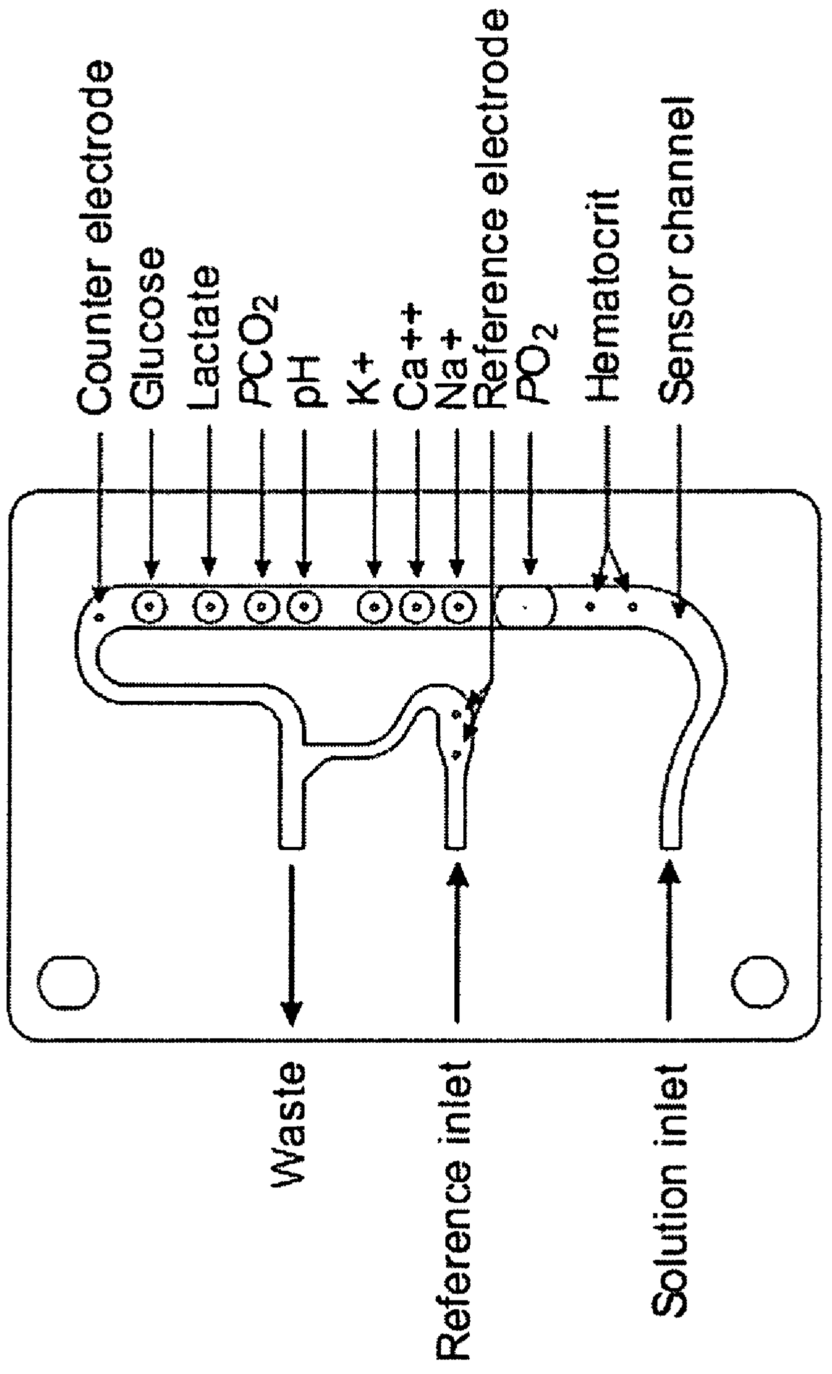
FIG. 17: Schematic of a multi-analyte flow sensor card in the GEM 3000 Analyzer

There are several well known blood gas analyzers in the market that use flow sensors. All of these analyzers require manual blood sampling (usually from the arterial line) to be presented to the sampling port of the analyzer. Multi-analyte electrochemical testing is done that include blood gases ($PCO_2$, $PO_2$), pH, metabolites (glucose, lactate, urea, creatinine), hemoglobin, and electrolytes. The blood sampling system of the present invention easily allows for integration of any of several flow sensors assemblies listed ahead, to carry out automated measurement for hospital bedside use. The first of these was called the Biostator, engineered in 1977 by Miles Laboratories of IN. A partial list of the existing blood gas/metabolite analyzers with trade names and associated companies include: ABL 80 (Radiometer, OH), GEM 3000 (Instrumentation Laboratory, MA), Rapidlab 400 (Siemens Diagnostics, NY), Cobas b221 (Roche Diagnostics, IN), Stat Profile (Nova Biomedical, MA), Proxima (Sphere Medical, UK), Combi Line (Eschweiler, Germany), Glukometer 3000 (BST Biosensors, Germany). FIG. 17 shows the schematic of one such flow-through multi-analyte sensor card of the GEM 3000 blood analyzer.

In place of a flow-sensor, a "needle" type sensor can be implanted in the inside lumen of the last tubing section (prior to the waste). Alternatively, these sensor wires could also be lodged in a flow-through fluidic system. These "needle" type sensors are currently used as subcutaneous continuous glucose monitoring systems. Current examples of such sensors with trade names and associated companies include: CGMS (Medtronic Minimed, CA), STS (Dexcom, CA), and Freestyle Navigator (Abbott, IL).

In a preferred embodiment a special feedback control feature is employed. An appropriate amount of insulin or dextrose is infused into the patient using the same pump and catheter by addition of a flow selection manifold. This manifold will default to saline, but will switch to dextrose (if glucose reading is low) or to insulin (if glucose reading is high) and infuse the appropriate dose as programmed into the system. In this arrangement, normoglycemia (typically between 80-110 mg/dl) will be maintained using the same set-up, further simplifying the work flow and minimizing errors associated with use of multiple systems and non-digital protocols.

The automated blood sampler and analyzer proposed above can be interfaced to existing patient monitors used in OR/ICU settings. Further, with the appropriate choice of the sensor, the system can also be used to perform automated monitoring of several other clinical situations. The goal being to improve patient outcomes by shortening the therapeutic turnaround time and increasing accuracy by reducing or eliminating pre-analytic error and specimen preparation. Some of these applications include: real-time sepsis monitoring (by early detection of cytokines and bacterial breakdown products); arterial oxygen status monitoring to potentially regulate the ventilators; coagulation status monitoring; and monitoring for pharmaceutical research on animal and human subjects.

All of the above descriptions are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

What is claimed is:

1. A system for automatically sampling blood from a patient, the system comprising: an intravenous blood access catheter; a tube set connected to the catheter forming a single passageway for transporting and dispensing blood samples from a patient to the end of the passageway at a point of measurement, which is in sensing communication with an external blood parameter sensor; a clamp-on air-bubble sensor and an occlusion sensor externally attached to the tube set; two 3-way pinch valves spaced apart and externally atached to the tube set and a single peristaltic pump externally attached to the tube set between said pinch valves; a rinse solution in fluid communication with both said pinch valves; and a controller operatively connected to the peristaltic pump and said pinch valves;

wherein the controller is configured to operate the peristaltic pump in forward and reverse mode, in forward mode, when the catheter is inserted in a patient's bodily fluid vessel, the peristaltic pump draws blood from the patient to the point of measurement, once the external sensor measures the blood analyte, the controller controls the pinch valves, releasing rinse solution, rinsing said passageway; after which the controller controls the pinch valves and operates the pump in reverse mode, re-infusing blood back into said patient.

2. The system in claim 1, wherein the system can be used for multiple automated diagnostic purposes, and integrated with a blood parameter monitor including a blood parameter sensor, wherein the blood parameter is selected from the group consisting of, glucose, lactate, electrolytes, colesterol, urea, and blood gases; wherein the blood parameter sensor is selected from the group consisting of, a test-strip, an electrochemical flow-through sensor, a mid-infrared spectroscopic flow-through sensor, a subcutaneous-implantable needle-type sensor inserted in said tube set in said passageway.

3. The system in claim 1, wherein the catheter is connected to the tube set via a specially designed luer connection, wherein the catheter comprises a patient end and a spaced apart end having a hub attached thereto; the luer connection has a first end, a barbed end spaced apart a distance L, and a cylindrical core having an inside diameter D, which is tapered at the point of transition to the barbed end; the luer first end is inserted inside the catheter hub; L and D are sized to eliminate the dead volume normally present when blood enters said catheter hub.

4. The system in claim 3, including an aseptic quick release connection attached to the tube set proximal to the luer connection, comprising a female port with a self sealing diaphragm, a male connector non-coring needle, and a leak proof negligible dead volume.

5. The system in claim 4, wherein the rinse solution is normal saline.

6. The system in claim 5, wherein the system can be configured to draw blood And dispense samples to the point of measurment, at predefined or user defined intervals.

7. The system in claim 6, wherein the catheter is a small gage catheter having a size of 22 ga, and the tube set cornprises micro tubing having a size of 0.5 mm ID.

8. The system in claim 7, wherein the length of tubing of the tube set ranges from 30 cm to 120 cm.

9. The system in claim 8, wherein the flow rate of the peristaltic pump ranges from 100 μL/min to 1000 μL/min.

10. The system in claim 9, wherein after the saline rinse, the controller is configured to operate the pump in reverse mode to re-infuse the unused blood back into the patient; after the blood is fully re-infused, the pump reduces speed to slowly infuse the patient with saline just enough to keep the vein open, preventing blood clotting; during this time the system is in standby or therapeutic infusion mode until the next predefined or user actuated measurement.

11. The system in claim 10, wherein the blood parameter is blood glucose, and the blood parameter sensor is a blood glucose sensor; and wherein the system includes a dextrose reservoir, an insulin reservoir, and a fluid selector manifold, for choosing the release of either saline, dextrose, or insulin; wherein the manifold defaults to saline, but will release dextrose, if the glucose reading is low, or release insulin, if the glucose reading is high.

12. The system in claim 11, wherein the pinch valves are actuated using a motor selected from the group consisting of, solenoid motors and piezoelectric motors; and wherein the system regulates the blood glucose using feedback control in a closed loop.

13. The system in claim 12, wherein the anticoagulant heparin of low-molecular weight variety is added to the saline.

14. The system in claim 12, wherein the passagewaay is covalently bonded with heparin.

15. A system for automatically sampling blood from a patient, the system comprising: an intravenous blood access catheter; a tube set connected to the catheter forming a single passageway for transporting and dispensing blood samples from a patient to the end of the passageway at a point of measurement, which is in sensing communication with an external blood parameter sensor, a clamp-on air-bubble sensor and an occlusion sensor externally attached to the tube set; an in-line dilution sensor inserted in the passageway near the point of measurement; two 3-way pinch valves spaced apart and externally attached to the tube set and a single peristaltic pump externally attached to the tube set between said pinch valves; a rinse sulution in fluid communication with both said pinch valves; and a controller operatively connected to the peristaltic pump and said pinch valves;

wherein the controller is configured to operate the peristaltic pump in forward and reverse mode, in forward mode, when the catheter is inserted in a patient's vein, the peristaltic pump draws blood from the patient to the point of measurement, once the external sensor measures the blood analyte, the controller controls the pinch valves, releasing rinse solution, rinsing said passageway; after which the controller controls the pinch valves and operates the pump in reverse mode, re-infusing blood back into said patient; the system is integrated with a glucose monitor in a closed loop with feedback control, the glucose monitor comprising, a test strip based glucose meter, a plurality of test strips, and means, for presenting a test strip in sensing communication with a blood sample at the point of measurement, and for ejecting a test strip after measurement; and the system includes a waste reservoir for collecting dispensed fluids and ejected test strips.

16. The system in claim 15, wherein upon a user activating the system, blood is drawn from the patient and dispensed to the point of measurement, until the blood is undiluted; after which flow is reversed for a very short duration such that that any hanging blood drop is pulled back to prevent untimely introduction of a blood sample on a test strip at the point of measurement.

17. The system in claim 16, wherein the glucose strip is auto-calibrated, wherein the controller operates the pump in forward mode dispensing a single blood sample onto the test strip for measurement; then the glucose meter measures the glucose concentration of the sample; spontaneously displaying the reading on a patient monitor; then the blood passageway is flushed with said rinse solution; then the pump reverses direction to re-infuse the unused blood back into the patient; after the blood is re-infused into the patient the pump reduces speed to slowly infuse the patient with the rinse solution just enough to keep the vein open, preventing blood clotting; during which time the system is in standby until the next predefined or user actuated measurement.

18. The system in claim 17, wherein the means for presenting a test strip in sensing communication with a blood sample comprises an automated strip handler, comprising: a resealable strip cartridge with opposed top and bottom ends, containing a plurality of strips stacked therein; the cartridge is open at the bottom end, and is weight loaded at the top pushing strips out of the bottom end;

a sliding strip feeding plate is capable of sliding to two positions, and comprises a projection with a size corresponding to the strip thickness; the cartridge bottom end and the base top surface are slidably attached and aligned so that the weight pushes a test strip onto the base plate while it is in the first position; three linear feed actuators; and a gripper arm with clamping gripper pads;

the first linear actuator slides the strip feeding plate towards the meter to the second position at the point of measurement and a second motor causes the gripper arm to securely clamp the test strip; the first linear actuator then slides the strip feeding plate back to position one;

the third actuator then moves the meter toward the test strip inserting the test strip inside the meter; then the gripper pads release the test strip, a blood sample is dispensed onto the test strip, and the meter measures the blood sample; then the third actuator causes the meter to eject the strip while the gripper holds and later releases the strip before it falls into the waste reservoir.

19. The system in claim 18, wherein the three linear feed actuators are powered by miniature motors selected from the group comprising, DC motors, stepper motors, and piezoelectric motors.

20. A method far automatically sampling at least one parameter of blood from a patient, wherein the system with feedback control is integrated with a test strip based glucose monitor having a glucose meter, a plurality of test strips and means for presenting test strips in sensing communication with a blood sample, using said system comprising: an intravenous blood access catheter, a tube set connected to the catheter forming a single passageway for transporting and dispensing blood samples from a patient to the end of the passageway at a point of measurement, which is in sensing communication with an external blood parameter sensor; a clamp-on air-bubble sensor and an occlusion sensor externally attached to the tube set; two three-way pinch valves spaced apart and externally attached to the tube set and a single peristaltic pump externally attached to the tube set between said pinch valves; a rinse solution in fluid communication with both said pinch valves; and a controller operatively connected to the peristaltic pump and said pinch valves, the method comprising the steps of:

a, before connecting the catheter to the tube set prime the tube set by rinsing the tube set with saline to remove all it bubbles;

b, via an aseptic detachable connection connect the tube set to the catheter;

c, when the catheter is inserted in a patient's vein, use the controller to operate the peristaltic pump in forward mode to draw blood from the patient to the point of measurement until the blood is undiluted;

d, use the controller to operate the peristaltic pump in reverse mode to pull back in the passageway any hanging blood droplet to prevent untimely suction of a blood sample by the test strip, thereby preventing said meter from giving an error message tiggered by a premature blood sample dispensed on the one of said test strips;

e, activate the means for presenting test strips in sensing communication with a blood sample to present one of said test strips for measuring a blood sample;

f, use the controller to operate the peristaltic pump in forward mode to dispense a blood sample onto one of said test strips presented using the automatic strip feeder;

g, use the meter to perforin the measurement;

h, discard the strip in the waste reservoir;

i, transmit the measured value to a display monitor through the communication protocol;

j, use the controller to open one of said pinch valves to release saline to clear the passageway of blood;

k, use the controller to operate the peristaltic pump in reverse mode to re-infuse the unused blood back into the patient;

l, use the controller to reduce the speed of the pump to slowly infuse saline into the vein to keep vein open before next measurement;

m, repeat above steps at a predefined or user defined frequency of measurement.

21. A system for automatically sampling blood from a patient, such that blood reinfusion is not required, the system comprising: an intrvenous blood access catheter, a tube-set connected to the catheter forming a single passageway for transporting and dispensing blood samples from a patient to the end of a passageway at a point of measurement, the blood pssageway being heparin coated and in sensing communication with an external blood parameter sensor; a clamp-on air-bubble sensor and an occlusion sensor externally attached to the tube set; a single three-way pinch valve and a single peristaltic pump externally attached to the tube set; a rinse solution; and a controller operatively connected to the peristaltic pump and the pinch valve; the controller is configured to first operate the pump and valve to draw blood from the patient, dispensing a blood sample to the point of measuement; then to operate the pump and valve to rinse said blood passageway to the waste.

22. The system in claim 21, wherein the system is configured to be used for multiple automated diagnostic purposes and integrated with a blood parameter monitor including a blood parameter sensor, wherein the blood parameter is selected from the group comprising: glucose, lactate, electrolytes, cholesterol, urea, and blood gases, wherein the blood parameter sensor is selected from the group comprising, a test-strip based glucose meter, a flow-through-sensor, a mid-infrared spectroscopic flow-through sensor, a subcutaneous-implantable, neede-type sensor inserted in said tube set in said blood passageway.

23. The system in claim 22, including one quick aseptic connect and disconnect mechanism having a leak proof negligible dead volume connection for connecting the catheter to the tube set; wherein the tubing is coated with heparin; wherein the rinse solution is normal saline; wherein there is a very short duration reverse pump flow cycle to pull back any hanging blood drop in the tube at the point of measurement to prevent premature suction by the test strip; wherein the system can be configured to draw blood and dispense samples to the point of measurement, at predefined or user defined intervals.

24. The system in claim 23, wherein the catheter is a small gage catheter having a size of 22 ga, and the tube set comprises micro tubing having a size of 0.5 mm ID; wherein the blood parameter is blood glucose, and the blood parameter sensor is a blood glucose sensor, wherein blood is sampled from a blood vessel from the group comprising, a peripheral vein, an arterial line, or central venous line; wherein the pinch valve is actuated using a motor from the group comprising, solenoid motors and piezoelectric motors; wherein an in-line dilution sensor inserted in the passageway near the point of measurement, the in-line dilution sensor is based on impedance measurement of the blood hematocrit level.

25. A system for automatically sampling blood from a patient, the system comprising: an intravenous blood access catheter; a tube set connected to the catheter forming a single passageway for transporting and dispensing blood samples from a patient to the end of the passageway at a point of measurement, which is in sensing communication with an external blood parameter sensor; a clamp-on air-bubble sensor and an occlusion sensor externally attached to the tube set; two 3-way pinch valves spaced apart and externally attached to the tube set and a single peristaltic pump externally attached to the tube set between said pinch valves; a rinse solution in fluid communication with both said pinch valves; and a controller operatively connected to the peristaltic pump and said pinch valves;

the catheter is connected to the tube set via a specially designed luer connection, wherein the catheter comprises a patient end and a spaced apart end having a hub attached thereto; the luer connection has a first end, a barbed end spaced apart a distance L, and a cylindrical core having an inside diameter D, which is tapered at the point of transition to the barbed end; the luer first end is inserted inside the catheter hub; L and D are sized to eliminate the dead volume normally present when blood enters said catheter hub;

an aseptic quick release connection attached to the tube set proximal to the luer connection, comprising a female port with a self sealing diaphragm, a male connector with a non-coring needle, and a leak proof negligible dead volume Design;

the catheter is a small gage catheter having a size of 22 ga, and the tube set comprises micro tubing having a size of 0.5 mm ID;

the length of tubing of the tube set ranges from 30 cm to 120 cm;

the flow rate of the peristaltic pump ranges from 100 μL/min to 1000 μL/min;

wherein the controller is configured to operate the peristaltic pump in forward and reverse mode, in forward mode, when the catheter is inserted in a patient's bodily fluid vessel, the peristaltic pump draws blood from the patient to the point of measurement, once the external sensor measures the blood analyte, the controller controls the pinch valves, releasing rinse solution, rinsing said passageway; after which the controller controls the pinch valves and operates the pump in reverse mode, re-infusing blood back into said patient;

the bodily fluid vessel is a vein; the rinse solution is saline; after the blood is fully re-infused, the pump reduces speed to slowly infuse the patient with saline just enough to keep the vein open, preventing blood clotting; during this time the system is in standby or therapeutic infusion mode until the next predefined or user actuated measurement;

the blood parameter is blood glucose, and the blood parameter sensor is a blood glucose sensor; the system includes a dextrose reservoir, an insulin reservoir, and a fluid selector manifold, for choosing the release of either saline, dextrose, or insulin; wherein the manifold defaults to saline but will release dextrose, if the glucose reading is low, or release insulin, if the glucose reading is high;

the pinch valves are actuated using a motor selected from the group consisting of, solenoid motors and piezoelectric motors; and the system regulates the blood glucose using feedback control in a closed loop;

an anticoagulant, heparin of low-molecular weight variety, is added to the saline.

* * * * *